US00PP10956P

United States Patent [19]

Lewis et al.

[11] Patent Number: Plant 10,956

[45] Date of Patent: Jun. 15, 1999

[54] HOP VARIETY NAMED 'COLUMBUS'

[75] Inventors: Gregory K. Lewis, Yakima; Charles E. Zimmermann, Prosser; Henry Hazenberg, Kennewick, all of Wash.

[73] Assignee: Hopunion USA, Yakima, Wash.

[21] Appl. No.: 08/409,908

[22] Filed: Mar. 22, 1995 (Under 37 CFR 1.47)

Related U.S. Application Data

[63] Continuation of application No. 08/159,859, Nov. 30, 1993, abandoned.

[51] Int. Cl.[6] ..... A01H 5/00

[52] U.S. Cl. ..... Plt./236

[58] Field of Search ..... Plt./100, 236

[56] References Cited

U.S. PATENT DOCUMENTS

| | | | |
|---|---|---|---|
| P.P. 8,812 | 6/1994 | Probasco | Plt./236 |
| P.P. 8,823 | 7/1994 | Probasco | Plt./236 |
| P.P. 8,824 | 7/1994 | Probasco | Plt./236 |

OTHER PUBLICATIONS

Defendant's First Motion for Partial Summary Judgment, dated Jun. 9, 1997.

Defendants' Memorandum of Points and Authorities in Support of Their First Motion for Partial Summary Judgement, dated Jun. 9, 1997.

Defendants' LR 56.1(a) Statement of Material Facts for Defendants' First Partial Summary Judgment Motion, dated Jun. 9, 1997 (without exhibits).

Plaintiff's Statement of Specific Facts in Opposition to Defendants' Motion for Partial Summary Judgment, dated Jun. 25, 1997 (without exhibits) (information subject to protective order redacted).

Plaintiff's Opposition to Defendants' First Motion for Partial Summary Judgment Motion, dated Jun. 25, 1997.

HopUnion's Response in Opposition to Defendants' Motion for Partial Summary Judgment, dated Jul. 8, 1997 (without exhibits).

Lewis, "The HopUnion U.S.A., Inc.—Low Trellis Hop Production System," Proc. Tech. Comm. of the IHGC of the XXXVIIIth International Hop Congress, Hereford, U.K. Published Rijksstation voor Landbouwtechniek, Merelbeke/Gent, Belgium, 17–37, 1990.

Kenny, Identification of U.S. Grown Hop Cultivars by Hop Acid and Essential Oil Analyses, *J. Amer. Soc. Brewing Chemists 48*(1):3–8, 1990.

Peacock and McCarty, "Varietal Identification of Hops and Hop Pellets," *Master Brewer Assoc. of the Americas Technical Quarterly 27*:81–85, 1992.

Nickerson and van Engel, "Hop Aroma Component Profile and the Aroma Unit," *Journal of American Society of Brewing Chemists 50*(3), 77–82, 1992.

American Society of Brewing Chemists, "α–Acids and β–Acids in Hops and Hop Extracts by HPLC (International Method)," in "Methods of Analysis," The Society, St. Paul, MN, 8th ed., 1992.

Hop Growers of America, Inc., 1991–1992 Annual Statistical Report, 37th Annual HGA Convention, Portland, Oregon, 1993.

*Primary Examiner*—Howard J. Locker
*Attorney, Agent, or Firm*—Seed and Berry LLP

[57] ABSTRACT

A new and distinct variety of hop, *Humulus lupulus* L., named Columbus, has a superior yield of cones and a superior content of alpha acids in its resin. The new variety was cultivated as a result of a cross at a nursery near Prosser, Wash., United States, and has been asexually reproduced in and about Yakima, Wash., United States.

5 Drawing Sheets

CROSS-REFERENCE TO RELATED APPLICATION

This application is a continuation of U.S. patent application Ser. No. 08/159,859, filed Nov. 30, 1993, now abandoned.

TECHNICAL FIELD

The field of the present invention is hops.

BACKGROUND OF THE INVENTION

Of conventional hop varieties, there are at least twenty named commercially grown hop varieties in the United States today, and some seventy-five to eighty varieties that are grown around the world. The varieties differ as to assorted physical features such as vine color and structure, as well as cone number, location, size and shape.

Commercial varieties of hop are female hops that exist as a perennial rootstock that produces an annual flush of above-ground, or aerial, vegetation. The perennial rootstock is comprised of a woody crown with a number of main roots and sub-roots that are used for water uptake, nutrient uptake, and winter starch storage. Over the winter, the woody crown supports many buds that develop into main vines (shoots) in the spring, emerge from the ground, and extend to produce the annual above-ground vegetation. In nature, with the onset of frosts in the fall, the above-ground portion of the plant "dies-back" to ground level, and only the perennial rootstock survives into the following year.

A main vine consists of a single flexible cylinder that produces pairs of leaves at nodes separated by variable distances along the length of the vine. The length of main vine between a pair of nodes is known as an internode. A bud is produced in the junction between leaf and vine, which junction is also known by the botanical term axil. Such a botanical term, as well as other botanical terms herein, are generally known to those of skill in the art, and can also be found in standard botanical texts such as Simon, E.W., et al., Lawson's Textbook of Botany—Revised, University Tutorial Press Ltd., London, England, 14th Ed. 1966. The bud grows and develops into a lateral, also known as a side-shoot or side-arm, with the same basic vegetative structure as the main vine. The buds on the laterals develop into groups of flowers that later mature into cones (strobiles). Because the laterals produce and support the cones of the hop, the structure of the laterals strongly influences the number of cones produced and hence the ultimate commercial yield of a variety.

The cones are the useful brewing commodity, and are referred to as "hops" in the commercial industry. Each cone is a group of flowers (inflorescence) consisting of sepals and petals (bracts and bracteoles) mounted on a central strig (or rachis). The resultant structure resembles a small pine cone or fir cone but is non-woody and green in color. In nature, the bracteoles support the seed of the plant.

Complete descriptions of the botanical structure of the hop plant are given in Burgess, "Hops—Botany, Cultivation and Utilization," Weed Crop Series, Interscience Publishers, Inc., New York, 1964 and Neve, "Hops," von Nostrand Reinhold, New York, 1991.

A trellis of poles and wire, commonly 18 feet in height and known as a "high trellis," supports strings that the main vines climb. The main vines grow to the top of the trellis, where they produce the laterals that support the groups of flowers that develop into the cones. Typically, the laterals bear cones only in the upper parts of the plant (i.e., closer to the main vine); the distance from the main vine varies from one variety to another. Under an alternative growing system, the "HopUnion Low Trellis Hop Growing System," the vines are grown on a trellis of single rows of 10 feet in height, like wine grapes (the 10 foot trellis is referred to herein as a "low trellis"). (Lewis, "The HopUnion U.S.A., Inc.—Low Trellis Hop Production System," Proc. Tech. Comm. of the IHGC of the XXXVIIIth International Hop Congress, Hereford, U.K. Published Rijksstation voor Landbouwtechniek, Merelbeke/Gent, Belgium, 17–37, 1990.) Under either system, when the cones are physiologically mature (ripe), the cones are harvested, then dried and compressed into bales for market, where the cones are typically used for the productuion of beverages such as beers, ales and related alcohol-containing liquids.

Different varieties of hops have differences in the chemical constituents of the lupulin of their cones. Accordingly, chemical analysis of such differences can be useful in distinguishing one hop variety from another. Such analysis is generally performed by high pressure liquid chromatography ("HPLC") of the soft resins along with gas liquid chromatography ("GLC") of the essential oils. Recently, Kenny developed a key for differentiation of hop varieties based on chemical analysis of the soft resins. (Kenny, "Identification of U.S. Grown Hop Cultivars by Hop Acid and Essential Oil Analyses," *J. Amer. Soc. Brewing Chemists* *48*(1):3–8, 1990.) Further, Peacock and McCarty, as well as Kenny, have developed keys for the differentiation of hop varieties based on chemical analysis of the essential oils. (Peacock and McCarty, "Varietal Identification of Hops and Hop Pellets," *Master Brewer Assoc. of the Americas Technical Quarterly* 27:81–85, 1992; Kenny, supra.) These keys are based on gross differences in the amounts of, and ratios between, major constituents, which differences are large enough to overcome variation inherent in the analytical analysis of biological material.

SUMMARY OF THE INVENTION

The present invention provides a new variety of hop (*Humulus lupulus* L.), which has been named 'Columbus'. The new variety comprises a superior yield of cones and, as discussed below, a superior content of alpha acids in its soft resins. Columbus is particularly suited for the production of beverages such as beers, ales and related alcohol-containing liquids.

DETAILED DESCRIPTION OF THE INVENTION

The present invention provides a new variety of hop (*Humulus lupulus* L.), named 'Columbus,' that has a superior yield of cones and a superior content of alpha acids in its soft resins. Columbus may be classed as a bitter hop (i.e., high in alpha acids content). Columbus was bred as the result of an open-pollination cross that was carried out in 1982 at a small hop nursery near Prosser, Wash. U.S.A. and was known by the identification number 9/17. Pursuant to growth, analysis, and testing, Columbus was identified and selected from numerous candidates arising from the cross. The exact parentage of Columbus is unknown. The breeding nursery that produced Columbus contained 20–30 female plants from which seed was collected en masse, and an approximately identical number of male plants were growing and flowering at the time that pollination occurred. Columbus is a diploid hop.

Set forth below are various characteristics that distinguish Columbus from conventional hop varieties. Columbus is initially distinguishable on the basis of its physical characteristics, including the location of its cones, the internode distance, number of cones per node, the yield of its cones, and the physical characteristics of the cones. Columbus is also distinguishable on the basis of its chemical characteristics, which are determined by chemical analyses of the soft resins and essential oils. Additionally, methods for asexual reproduction of Columbus are discussed.

I. Physical Characteristics of Columbus

A. Location of Cones

Figure 1:
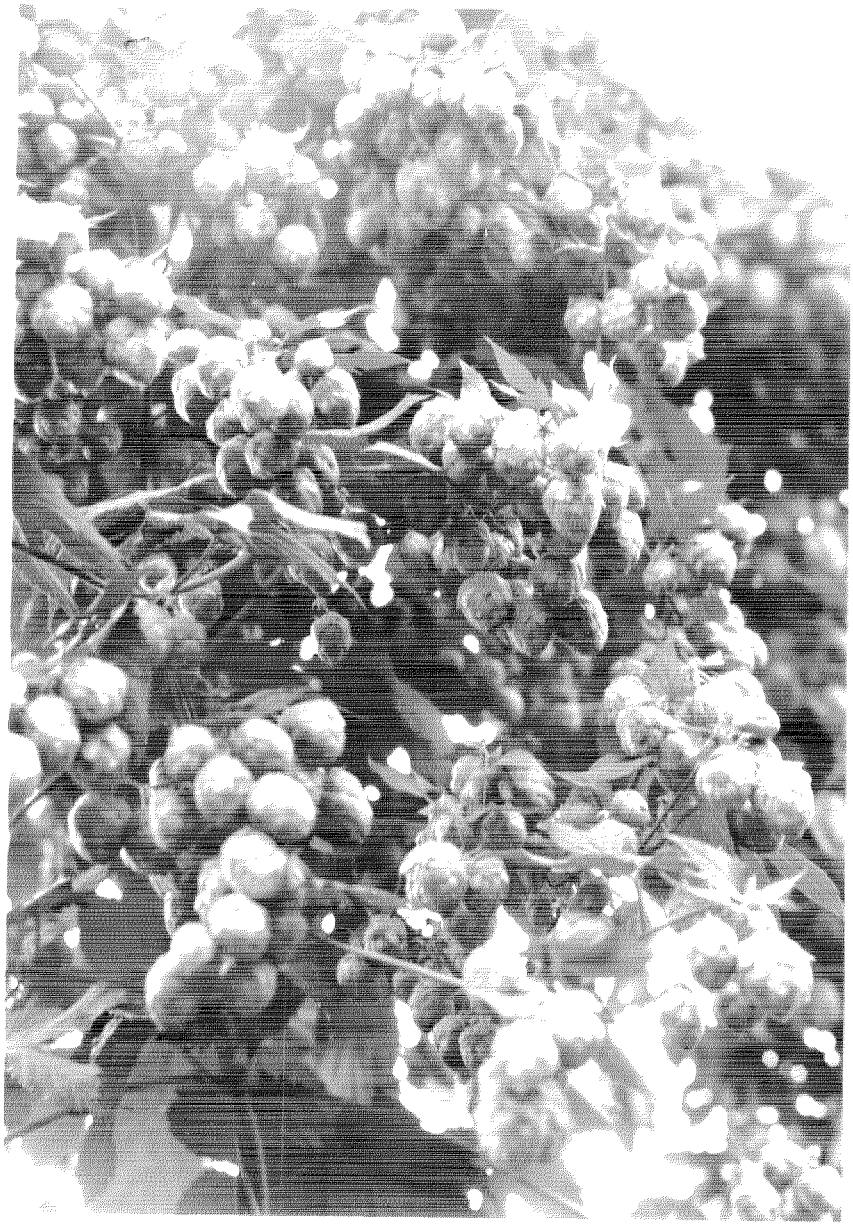
FIG. 1 depicts a section of Columbus vine near harvest.

Columbus bears a high number of cones on its laterals down to a height of about 4 feet from the ground, when grown on a high trellis. A close-up Figure depicting in detail the vine structure of Columbus is presented as FIG. 1. Conversely, most conventional hop varieties on a high trellis do not bear significant numbers of cones below about 8 feet from the ground.

Figure 2:
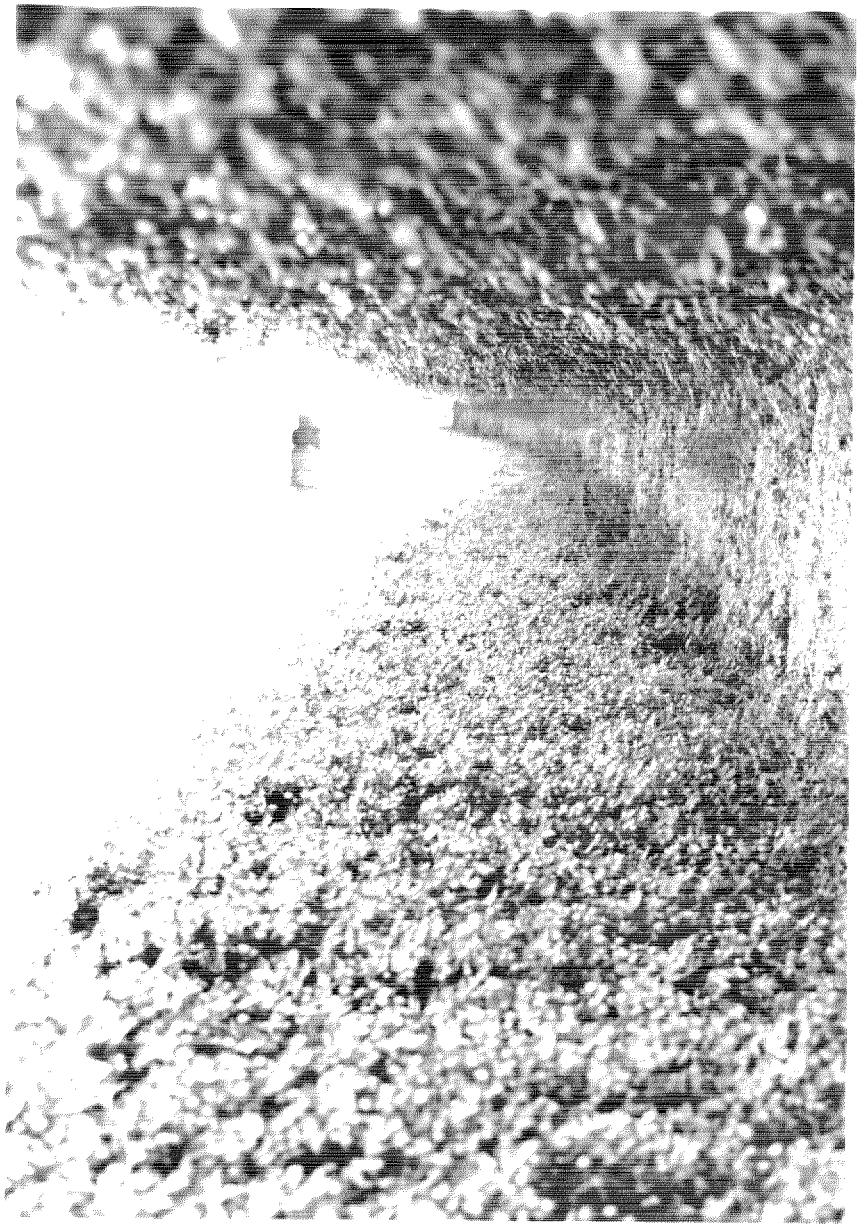
FIG. 2 depicts a low trellis planting of Columbus.

On a low trellis, Columbus produces significant numbers of cones down to ground level, and cones can even be found on untrained side-shoots running along the ground. (FIG. 2.) Conversely, most conventional hop varieties on a low trellis produce cones down to about 4 to 8 feet from the ground.

B. Internode Distance

Figure 3:
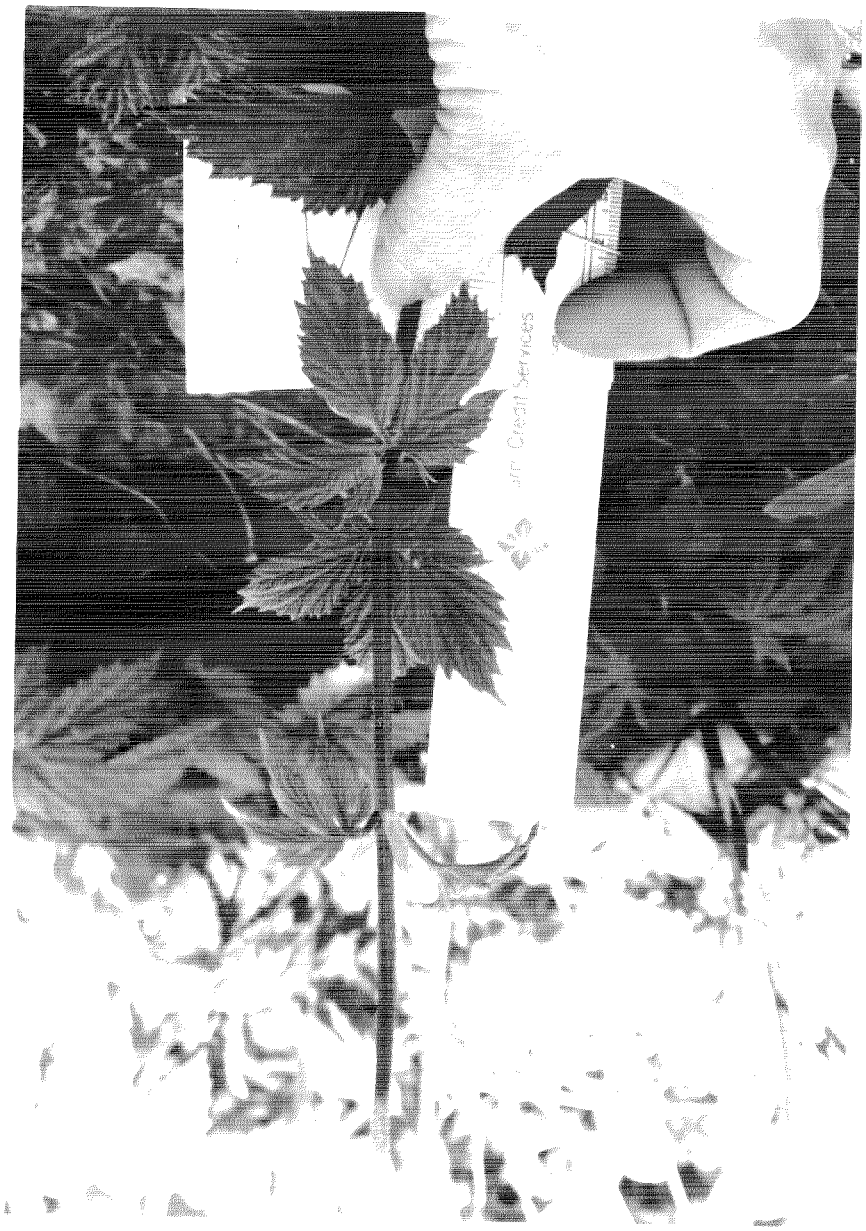
FIG. 3 depicts early season growth of Columbus with an internode length of about 3 inches.

The internode distance on a main vine of any hop variety is important to the yield of cones because the shorter the internode length, the greater the number of yielding laterals for a given length of main vine. Columbus has a shorter than average mature internode length, about 8" to 12", with an early season internode distance of about 3". (FIG. 3.) Conversely, in conventional hop varieties such as Nugget, the mature internode length varies from 10" to 16", with an early season internode distance of about 8". There are also "dwarf hops" in which the mature internode length varies between 5" to 8".

C. Growth Characteristics

Although the early season growth rate and length of time for hop vines to reach the top wire of a trellis vary widely due to factors such as climatic conditions and growth and harvest management, the early season growth of Columbus is generally faster than the most aroma hops (such as Tettnang, Perle, Centennial, Saaz, Spalt, Mt. Hood, Liberty, Hallertau, Hersbruck, and Fuggle), and also faster than the quicker-growing aroma hops such as Cascade and Willamette. Such aroma hops are generally first trained between May 7 and May 10, and reach the top wire between June 20 and June 30. The aroma hop Cluster and the bitter hops Galena and Chinook are typically trained about May 15 and reach the top wire from about June 20 to about June 30. The bitter hops Nugget, Olympic, Eroica, and Columbus are typically trained about May 25 and reach the top wire about June 27 to about July 7. Among this latter group, Columbus typically grows slower than the other hop varieties at first, but then accelerates its growth and can grow to the top faster than Nugget on occasion. In other words, Columbus is a late maturing hop, and has an early growth rate that is typical for bitter hops and for Cluster, but it is a slow starter.

D. Habit

In common with most other hop varieties, the main vines of Columbus are originally green in color but turn to dark red to purple as the season progresses. The main vines are ridged, and along the ridges are hooked hairs that adhere to the supporting trellis. A characteristic feature of Columbus vines, as discussed above, is the short internodes.

Although the lateral length of a hop variety can vary greatly due to factors such as climate and management practices, the laterals of Columbus are typically longer than those of aroma varieties, are typically similar in length to those of Galena and Nugget, and are typically shorter than Cluster, Chinook, Olympic and Eroica. A generalization of comparative lateral lengths is as follows:

TABLE 1

| Hop Variety | Length of Lateral |
|---|---|
| Mt. Hood, Liberty, Saaz, Spalt, Perle, Hallertau, Tettnang, Hersbruck, Fuggle, Centennial | 1'–2' |
| Cascade, Willamette | 1.5'–2.5' |
| Columbus, Galena, Nugget | 2.0'–3.0' |
| Cluster, Chinook, Olympic, Eroica | 2.5'–3.5' |

Although most commercial hops have longer laterals in the head and much shorter laterals in the lower reaches of the vine. Columbus tends to have approximately even length laterals along the length of the vine. The sub-branches of the laterals develop as bunches of cones, and as set forth below, Columbus has an unusually high number of cones in each lateral bunch, typically greater than any other commercial variety.

The head of the vine is also subject to variation depending on such factors as climatic conditions and management practices, but Columbus can be generally grouped with Cascade, Willamette, Nugget and Galena as having a moderate head, although the head of Columbus is slightly smaller and neater than typical. The head of Columbus also appears more dense than most other varieties, apparently because more laterals are developed from an equivalent vine length due to the short internode distance discussed above.

In terms of overall vine morphology, Columbus tends to be stronger than the aroma varieties but slighter than the other bitter hops and Cluster. As noted above, the overall vine morphology also gives the appearance of being more dense than other commercial hop varieties.

E. Leaf Morphology

The leaf morphology of Columbus is typical for most commercial hop varieties, and may be summarized as set forth in the table below.

TABLE 2

| Character | Early Main Vine Leaves | Late Main Vine Leaves | Lateral Leaves |
|---|---|---|---|
| Number | 2/node | 2/node | 2/node |
| Lobes | cordate - 3 | 35 | cordate - 3 |
| Width | 3–5" | 4–7" | 1–2" |
| Length | 3–5" | 4–7" | 1–2" |
| Upper Surface Texture | smooth | smooth | smooth |
| Lower Surface Texture | fairly rough | rough | slightly rough |
| Color | med-dark green | dark green | med-dark green |
| Margins | lightly serrated | moderately serrated | lightly serrated |

The leaf color of Columbus is also similar to other commercial hop varieties, although in the early part of the growing season when Columbus is slower growing than other bitter hops and Cluster, Columbus has a darker leaf, while later in the season when Columbus is faster growing, the leaf of Columbus is similar to other hops in its class. The leaf of Columbus is typically not as dark as most of the slower growing aroma hops.

F. Number of Cones per Node

Figure 4:
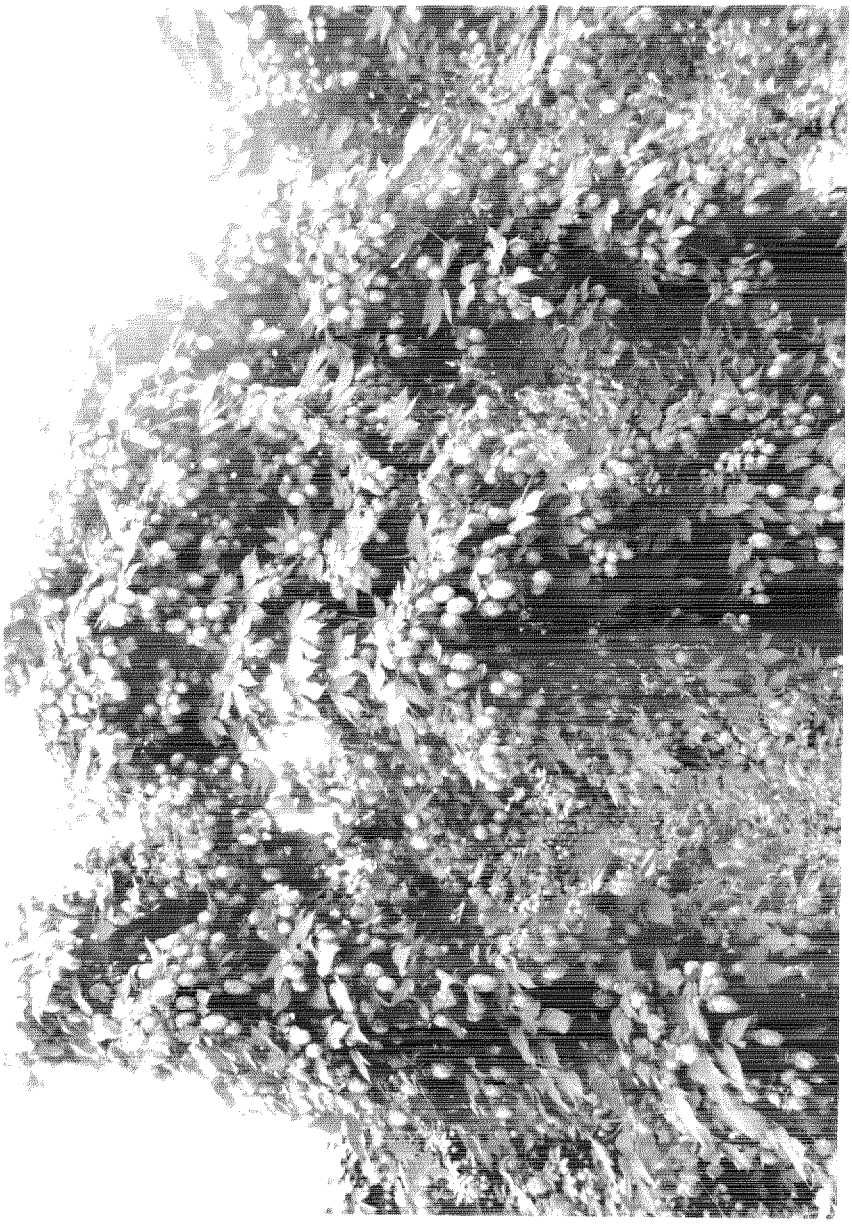
FIG. 4 depicts Columbus on a low trellis and shows the density of the cones in the canopy (cones per lateral node).

Typically, cones are found in high number clusters borne at nodes on a lateral that are close to the main vine ("basal lateral nodes"). Progressively fewer cones are found in the clusters located at nodes progressively farther away from the main vine. Ultimately, the lateral terminates in a tip bearing a single cone. Columbus yields a high number of cones at the basal lateral nodes as well as at nodes located farther away from the main vine. (FIG. 4.) The basal lateral nodes of Columbus have produced up to 42 cones. Conversely, conventional low yielding hop varieties typically bear clusters of about 8–16 cones at basal lateral nodes, while conventional high yielding varieties typically bear clusters of about 16–28 cones at basal lateral nodes.

G. Yield of Cones

Due to the above discussed characteristics, Columbus provides an outstanding hop variety comprising the following: a plant bearing cones much lower down the main vine; a reduced internode length on the main vine, which results in a greater number of yielding laterals per given length of main vine; and, greater numbers of cones at each node, which results in greater numbers of cones on each of the yielding laterals. Accordingly, Columbus produces an outstanding yield of cones, whether grown on a high trellis or a low trellis.

Yield data for many hop varieties are compared with yield data for Columbus in Table 3. All hops were grown on a high trellis.

TABLE 3

| Variety | Washington State Five-Year Average Yield (lb/acre) | HopUnion 1992 Average Yield (lb/acre) |
|---|---|---|
| Low yielding varieties | | |
| Perle | 1172 | 1366 |
| Tettnang | 970 | 1140 |
| High yielding varieties | | |
| Cluster | 2018 | 2407 |
| Chinook | 1938 | 2216 |
| Nugget | 1950 | 2829 |
| Galena | 1926 | 2502 |
| Columbus | — | 3290 |

(Hop Growers of America, Inc., 1991–1992 Annual Statistical Report, 37th Annual HGA Convention, Portland, Oreg., 1993.)

Below in Table 4, yield data from low trellis hops grown at HopUnion farms for 1990 and 1992 are compared with experimental yield data for Columbus from 1991 and 1992.

TABLE 4

Yield Data for Low Trellis Hops

| Variety | 1990 Average Yield (lb/acre) | 1992 Average Yield (lb/acre) |
|---|---|---|
| Perle | 1557 | 1010 |
| Tettnang | 1062 | 800 |
| Cascade | 1415 | 1570 |
| Chinook | 1234 | 1017 |
| Nugget | 1712 | 1175 |
| Galena | 1800 | 1500 |
| | (Year: 1991) | |
| Columbus | 2832 | 3408 |

First year plantings of hops typically yield significantly less than mature plantings of the same varieties. However, a 1992 first year planting of Columbus on a low trellis yielded, over an area of about 4.5 acres, an average of 2547 lb/acre. Columbus produces such yields with a growth habit that presents no problems for ease of harvesting.

H. Physical Characteristics of the Cones

Cones are typically described by size (large, medium, or small) and by degree of compactness (loose, medium, or tight). Size and compactness are indicative of the degree of compression (internode length) between the nodes of the central strig that subtends (supports) the bracts and bracteoles. Also, cones are often described in terms of weight, most often expressed in milligrams (mg). Light cones are usually between 120 and 160 mg in weight, heavy cones usually between 160–220 mg (kiln dry basis). Often the description includes a brief comment on general shape of the cone, such as round, ovoid, plump, etc.

Figure 5:
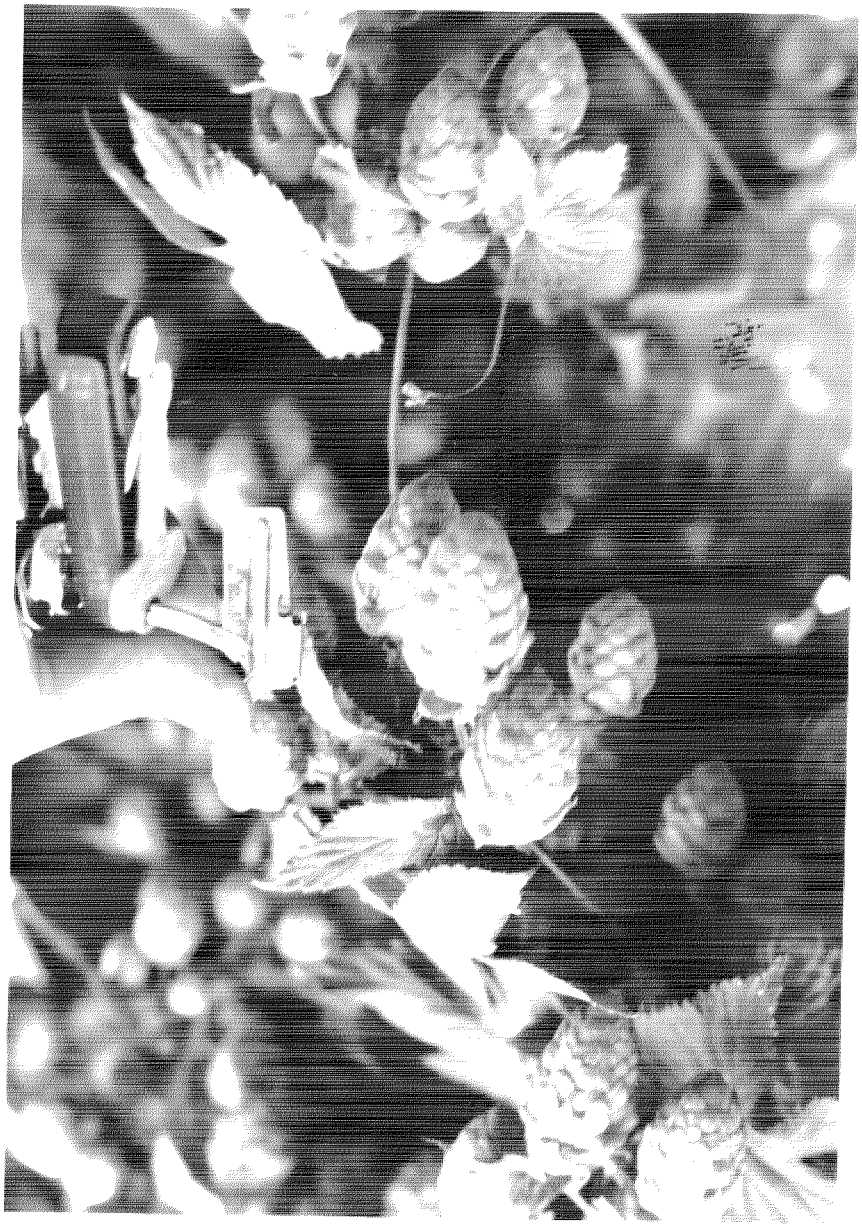
FIG. 5 depicts the physical appearance of Columbus cones.

Columbus cones are normally medium in length, typically about 1.25", medium to tight in compactness, and typically about 1" in diameter. Further, Columbus cones are typically quite rounded and plump, and weigh about 180–250 mg (kiln dry basis) at maturity. (FIG. 5.) Conversely, Chinook cones typically have bracts with the tips turned backwards (reflexed). Fuggle cones are typically square in cross-section. Nugget cones are typically compact, tight, and firm. Columbus cones are typically more dense than other commercial hop varieties, and hence typically heavier on a per cone basis. Columbus cones have little or no propensity to shatter when fresh or when properly dried.

I. Disease and Pest Resistance

The susceptibility of Columbus to downy mildew (*Pseudoperunospora humuli*) is similar to Galena and Cluster, which are less resistant than most other commercial hop varieties. Columbus is apparently resistant to Verticillium wilt (*Verticillium dahliae*). Tests have indicated that Columbus can become infected with *Prunus necrotic* ringspot virus, hop latent virus and American hop latent virus, although it is also possible to free Columbus of these viruses by standard meristem culture techniques. Columbus has not shown any symptoms of infection when carrying these viruses, as is usual for most commercial hop varieties. Columbus shows no unusual tolerance or sensitivity to damson hop aphid (*Phorodon humuli*) and two spotted mite (*Tetranychus urticae*).

J. Quality Profile

Based upon sensory analyses of dried/baled leaf hop samples, Columbus has a quality profile that is similar to most other commercial hop varieties. Columbus has a mild, gentle aroma with no particular, peculiar character. However, Columbus is distinguishable from the commercial aroma varieties and Cluster by virtue of its higher resin content, which is indicated by visual inspection of the open cone and the much greater number of lupulin glands present in Columbus.

II. Chemical Characteristics of Columbus

A. Chemical Analyses in General

Chemical analysis of hops typically consists of analysis of the lupulin of the cones. The lupulin consists of the following chemical components and sub-components:

| | |
|---|---|
| Soft resins | alpha acids (humulones)<br>beta acids (lupulones) |
| Hard resins | |
| Uncharacterized resins | |
| Waxes | |
| Tannins | |
| Essential oils | hydrocarbons<br>oxygenated compounds<br>sulfur compounds |

Of the above components, the soft resins and essential oils are of particular relevance to the differentiation of hop varieties. In regard to the soft resins, there are three analogues of the alpha acids, i.e., humulone, ad-humulone, and cohumulone, and there are also three analogues of the beta acids, i.e., lupulone, ad-lupulone, and colupulone.

Due to their chemical characteristics, some hop varieties are referred to as aromatic, or low alpha, hops and are known to contribute good hop flavor and aroma. Other hop varieties are high in bittering potential (i.e., high in alpha acids) and are referred to as bitter or high alpha hops. Columbus may be referred to as such a bitter or high alpha hop. Hop varieties in an intermediate varietal classification have medium levels of alpha acids and are referred to as dual-purpose hops.

B. Soft Resin Characteristics

Table 5 lists the total amount of alpha and beta acids, the ratio of alpha acids to beta acids, and estimates of the relative proportions of cohumulone and colupulone for several high alpha hops. This data was determined by HPLC analysis according to standard methods well known to those having skill in the art. (See, e.g., American Society of Brewing Chemists, "Hops Method 12: Analysis of Hops, Hop Powders and Hop Pellets by High Pressure Liquid Chromatography," in "Methods of Analysis," The Society, St. Paul, Mn., 8th ed. 1991.) Table 5 also gives data on storage losses, which indicate the loss of alpha acids by oxidation. The data are expressed as ranges to account for inherent biological variation from sample to sample.

TABLE 5

| Parameter | Chinook | Nugget | Galena |
|---|---|---|---|
| Alpha acids (% w/w) | 12.0–14.0 | 12.0–14.0 | 11.0–13.0 |
| -cohumulone (%) | 30–35 | 24–30 | 36–42 |
| Beta acids (% w/w) | 3.4–4.0 | 4.0–5.5 | 7.0–9.0 |
| -colupulone (%) | 55–66 | 50–55 | 60–65 |
| Alpha/beta ratio | 3.5–4.0 | 2.5–3.0 | 1.5–2.0 |
| Oil content (mls/100 g) | 1.5–2.3 | 1.2–2.0 | 0.7–1.2 |
| Loss of alpha acids (%) -6 months storage room temperature | 35–45 | 20–35 | 20–30 |
| **Parameter** | **Olympic** | **Eroica** | **Columbus** |
| Alpha acids (% w/w) | 11.5–13.5 | 11.0–13.0 | 14.0–16.0 |
| -cohumulone (%) | 27–34 | 38–43 | 30–35 |
| Beta acids (% w/w) | 4.0–6.0 | 4.0–5.5 | 4.5–5.5 |
| -colupulone (%) | 57–62 | 67–70 | 55–60 |
| Alpha/beta ratio | 2.0–2.7 | 2.2–2.8 | 2.7–3.3 |
| Oil content (mls/100 g) | 1.4–2.0 | 0.5–1.3 | 1.5–2.2 |
| Loss of alpha acids (%) -6 months storage room temperature | 40–55 | 35–50 | 60–80 |

Table 5 indicates the following: (a) Columbus has a higher content of alpha acids than the other high alpha hops; (b) Columbus' cohumulone and colupulone contents are higher than Nugget, lower than Eroica and Galena, and similar to Chinook; (c) Columbus' beta acid content is higher than Chinook and lower than Galena; (d) Columbus' alpha/beta ratio is higher than Galena or Olympic but lower than Chinook; and (e) Columbus more rapidly loses its alpha acids in ambient storage than the other varieties.

Table 5 shows that Columbus has an alpha acids content well in excess of 10% w/w. This distinguishes Columbus from the aromatic hops. Examples of such aromatic hops are listed in Table 6.

TABLE 6

| Variety | Alpha acids content (% w/w of cone) |
|---|---|
| Cascade | 4.5–7.0 |
| Cluster | 5.5–8.5 |
| Fuggle | 4.0–5.5 |
| Hallertau | 3.5–5.5 |
| Hersbruck | 3.5–5.5 |
| Liberty | 3.0–5.0 |
| Mount Hood | 5.0–7.5 |
| Perle | 7.0–9.5 |
| Saaz | 3.0–4.5 |
| Spalt | 3.0–5.5 |
| Tettnang | 4.0–5.0 |
| Willamette | 4.0–6.0 |

As discussed above, Kenny developed a key for identification of hop varieties based on the soft resin components. The application of the key of Kenny to Columbus is depicted in Table 7. At each decision point, certain varieties are eliminated according to a yes/no decision. The path to Columbus is shown by the double arrow. In the key depicted in Table 5, as well as in the other keys discussed herein, steps from the published key that did not eliminate any varieties in the present analysis have been deleted.

TABLE 7

| | | | Major U.S. Variety Eliminations |
|---|---|---|---|
| 1. Fresh alpha + beta > 15% and Fresh Alpha > 10% | → | NO | Cascade, Cluster, Fuggle, Hallertau, Hersbruck, Liberty, Mt. Hood, Perle, Saaz, Spalt, Tettnang, Willamette |
| YES (High alpha hops) | | | |
| 2. Cohumulone > 40% | → | YES | Eroica |
| NO | | | |
| 3. Colupulone > 60% | → | YES | Galena |
| NO | | | |
| 4. Cohumulone < 30% | → | YES | Nugget |
| NO | | | |
| 5. Alpha/beta ratio > 3.0 | → | YES | Chinook (3.5–4.0) |
| | → | NO | Olympic (2.0–2.7) |
| Columbus(2.7–3.3) | | | |

Table 7 relates to hops with a hop storage index, or HSI, well below 0.300, which indicates that the alpha and beta acids of the hops are fresh when analyzed. In Table 7, step 1 eliminates all the aromatic hops on the basis of their low content of alpha acids and low alpha plus beta acids. Step 2 eliminates Eroica on the basis of high cohumulone content. Step 3 eliminates Galena on the basis of high colupulone content. (Eroica is again eliminated at this step.) Step 4 eliminates Nugget on the basis of low cohumulone content. Step 5 eliminates Chinook on the basis of a high alpha/beta ratio, while Olympic is eliminated on the basis of a low alpha/beta ratio. Note, Chinook is also eliminated on the basis of its higher beta acid content.

Accordingly, Columbus is differentiated from all major U.S. varieties based on its soft resins content. Similarly, Columbus is distinguished from the minor U.S. hop varieties, except Aquila, Banner, and Centennial, based on soft resins content. However, Columbus is distinguished from Aquila, Banner, and Centennial by its essential oils content, as discussed below.

C. Essential Oils Characteristics

Detailed analysis of the essential oils allows a further differentiation of Columbus from other hops. Table 8 further distinguishes some of the varieties discussed above in Table 7, while Table 9 distinguishes varieties not distinguished above.

Extraction and analysis of essential oils are performed according to methods well known to those having skill in the art. Preferably, the essential oils are extracted by steam distilling previously dried hops for about four hours (with the steam of the distillation condensed using a cold-finger condenser). The resultant essential oils are then examined by GLC analysis.

GLC analysis for various hops are presented as Appendices 1 and 2 hereto as follows:

Appendix 1: Detailed essential oil analysis results of many of the world's hop varieties including all U.S. grown varieties except Mount Hood. Columbus is the final entry.

Appendix 2: Detailed GLC traces and listings of constituent peaks from essential oils analysis. Columbus is compared with the other U.S. high alpha hops, Galena, Chinook, and Nugget.

As with the soft resins, keys can be used to differentiate by essential oils content. Only United States varietal differentiations are depicted below in Tables 8 and 9, but non-United States varietal eliminations are listed in Peacock and McCarty, supra, and can be readily utilized by those having skill in the art to distinguish between those varieties and Columbus.

TABLE 8

Key of Kenny

| | | | Major U.S. variety eliminations |
|---|---|---|---|
| 1. β-Farnesene content > 1% | → | YES | Cascade, Fuggle, Saaz, Spalt Tettnang, Willamette |
| NO | | | |
| 2. Humulene/ β-Caryophyllene ratio > 1.5 | → | NO | Eroica, Olympic |
| YES | | | |
| 3. Presence of 2-Tridecanone/ presence of a peak @ 34.38 > 1.0% | → | NO | Galena (*see note in text) |
| NO | | | |
| 4. β-Caryophyllene/ -copaene > 20 | → | YES | Cluster, Nugget |
| NO | | | |
| Chinook (12.1) Columbus (13.4) | | | |

Table 8 was prepared using the data provided in Appendix 1. As shown in Table 8, step 1 eliminates the high β-farnesene hops, i.e., Cascade, Fuggle, Saaz, Spalt, Tettnang, and Willamette. Step 2 eliminates the low humulene varieties, i.e., Eroica and Olympic. Step 3 eliminates Galena because Columbus is unique for having no 2-tridecanone, and Columbus lacks a large peak found in Galena at 34.38 minutes (the peak is greater than 1% of the measured components of Galena). Step 4 eliminates both Cluster and Nugget. The remaining varieties are Columbus and Chinook. As shown in Table 7, Columbus is differentiated from Chinook by Columbus' lower alpha/beta ratio. In regard to some other varieties, Perle is eliminated by virtue of its low alpha acids content, while Columbus is distinguishable from Hersbruck, Hallertau, Liberty, and Mount Hood because Columbus has a much higher alpha acids content.

TABLE 9

Key of Peacock and McCarty (1992)

| | | | Major U.S. variety eliminations |
|---|---|---|---|
| Columbus | | | |
| 1. Humulene present | → | YES | Aquila, Eroica |
| YES | | | |
| 2. β-Farnesene > 5% Humulene | → | YES | Cascade, Fuggle Saaz, Spalt, Tettnang, Willamette |
| NO | | | |
| 3. Humulene/Selinene > 20 | → | YES | Banner, Hallertau, Liberty, Mt. Hood, Perle |
| NO | | | |
| 4. Contains Eudesmol | → | YES | Chinook, Hersbruck |
| NO | | | |
| 5. Cohumulone < 38% | → | NO | Cluster, Galena |
| YES | | | |
| Columbus, Nugget, Olympic | | | |

Table 9 depicts the key of Peacock and McCarty, which differentiates Aquila, Banner, and Centennial. The data from Appendix 1 is used for all steps except step 4, for which the data in Appendix 2 (which quantifies eusdesmol) is necessary. In Table 9, Step 1 eliminates Aquila and Eroica. Step 2 eliminates the six high β-farnesene hops. Step 3 eliminates Perle, Banner, Hallertau, Liberty, and Mount Hood. Step 4 eliminates Hersbruck and Chinook. Step 5 eliminates Cluster and Galena. Table 7 does not distinguish Columbus from Nugget and Olympic. However, as discussed above, Nugget and Olympic are distinguished from Columbus by each of Table 7 and Table 8.

Finally, the variety Centennial has not yet been distinguished. The data in Appendix 1 show that Centennial has a β-caryophyllene level of 2.649, while Columbus has a β-caryophyllene level of 10.236. Therefore, the varieties are distinguished because they are at virtually opposite ends of the scale for β-caryophyllene.

III. Asexual Reproduction (Propagation) of the Plant

Columbus is asexually reproduced according to methods well known to those having skill in the art. Such methods generally comprise one of three procedures: (a) taking rootstock cuttings known as "roots" or "strap cuts;" (b) converting vine material into woody root-like material in the field and dividing this material into "layered cuttings;" or (c) the use of softwood cuttings, which are also known as "mist cuttings," of green vegetative or shoot material, usually under greenhouse conditions. Further, traditional methods can be applied to make a cell tissue culture from Columbus. Such a cell tissue culture can be stored for extended periods, and gives rise to clones (i.e., asexual progeny) of Columbus. Columbus has been asexually reproduced on ranches associated with HopUnion USA, Inc., located in and about Yakima, Wash. U.S.A.

A. Asexual Reproduction by Taking Rootstock Cuttings

In the field, when main vines die back in the fall, their bases turn woody and swell with the deposition of starch reserves. These bases produce buds at the sites where the main vine nodes were previously located. The bases, usually 4"–8" long and between one-half and two inches thick, are removed by cutting with a sharp knife; other buds on the rootstock produce re-growth in the spring. The detached vine bases are then planted singly or in multiples, in pots or in the field.

Such a procedure typically provides up to a 15-fold increase over the starting number of plants. The increase may be lower where multiple rootstocks (up to 6–8) are to be planted at a single site, to form a single new composite plant.

B. Asexual Reproduction by Layered Cuttings

In the field, main vines are grown up a string, typically to a pre-determined height of about 10 feet. The string is then lowered and the newly grown main vines laid along the ground (for example, for about 8 feet). The string is then re-hung so that a portion of the main vines can renew vertical growth, but in a new location. Some main vines are left laying along the ground and are buried with soil, where the absence of light on the buried, green main vine stimulates it to turn woody, form buds at the nodes and swell with starch deposits. When the unburied portion of the vine has died back, the buried, now woody, portion is dug up and cut up into numerous layered cuttings, which are then replanted to give new plants. Such a procedure provides up to about a 50-fold increase over the starting number of plants.

In an alternative embodiment, new plants are placed at the bottom of deep, open trenches, preferably in a nursery. As the plants grow, soil is periodically pushed into the trench around the vines, thereby yielding layered cuttings in a vertical plane.

C. Asexual Reproduction by Softwood (Mist) Cuttings

Actively growing main vines of a plant are cut into sections comprising a half-node, a single node, or two nodes. Main vines for this purpose are preferably grown in a greenhouse, where growing conditions can be maximized. The cuttings are planted and stuck in a suitable medium, preferably with bottom heat and an intermittent water mist, further preferably under glass. The cuttings produce a rooted plant with new main vine growth about two to three weeks after removal from the original plant. These rooted softwood cuttings can be further grown in pots, in a nursery, or even in the final new plantation. Using such a procedure, it is possible to achieve up to about a 100-fold increase over the starting number of plants.

APPENDIX 1

Detailed GLC analysis of assorted hop varieties.
Analytical Conditions: see Kenny (1990), supra.
OIL AREA PERCENTS OF COMMERCIAL HOPS

| GC/ FID RT. | CMPD. # | TENTATIVE IDENTIFICATION BY GC/ MASS SPECTROSCOPY | 21223 AQUILA | 21053 AURORA |
|---|---|---|---|---|
| 6.42 | 9 | A-PINENE | 0.105 | 0.112 |
| 7.46 | 14 | ISOBUTYL ISOBUTYRATE | 0.000 | 0.326 |
| 8.10 | 16 | 8-PINENE | 0.898 | 0.817 |
| 9.11 | 18 | MYRCENE | 62.462 | 58.731 |
| 9.77 | 22 | 2-METHYL-BUTYL PROPANOATE | 0.171 | 0.159 |
| 9.90 | 23 | ISOAMYL ISOBUTYRATE | 0.000 | 0.076 |
| 9.96 | 24 | 2-METHYL-BUTYL ISOBUTARATE | 0.370 | 0.754 |
| 10.28 | 26 | L-LIMONENE | 0.243 | 0.228 |
| 10.62 | 27 | B-PHELLANDRENE? | 0.262 | 0.234 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| | | C10H15 | | |
| 11.59 | 32 | trans-OCIMENE | 1.542 | 0.207 |
| 12.45 | 35 | 2-METHYL-BUTYL 2-METHYL-BUTYRATE | 0.000 | 0.000 |
| 12.68 | 36 | METHYL HEPTANOATE | 0.445 | 0.656 |
| 12.91 | 40 | ISOAMYL ISOVALERATE | 0.000 | 0.000 |
| 14.31 | 43 | METHYL 4-METHYL-HEXA-2-ENOATE | 0.069 | 0.160 |
| 14.39 | 45 | METHYL 6-METHYL-HEPTANOATE | 0.230 | 0.264 |
| 15.98 | 51 | METHYL OCTANOATE | 0.317 | 0.506 |
| 16.26 | 55 | NONANAL | 0.048 | 0.083 |
| 19.41 | 73 | METHYL NONANOATE | 0.172 | 0.343 |
| 19.56 | 75 | 2-DECANONE, A-YLANGENE | 0.139 | 0.379 |
| 19.93 | 77 | A-COPAENE | 0.121 | 0.161 |
| 21.00 | 83 | LINALOOL | 0.368 | 0.997 |
| 21.31 | 88 | A-GURJUNENE | 0.000 | 0.000 |
| 21.42 | 89 | 7-METHYL-2-DECANONE | 0.062 | 0.218 |
| 22.56 | 93 | C15H24 CALARENE? | 0.000 | 0.000 |
| 22.72 | 95 | A-BERGAMOTENE, METHYL DECANOATE | 0.239 | 0.408 |
| 23.01 | 96 | 2-UNDECANONE | 0.448 | 1.402 |
| 23.10 | 97 | 2-DECANOL | 0.000 | 0.160 |
| 23.44 | 99 | 8-CARYOPHYLLENE | 4.104 | 4.403 |
| 23.84 | 102 | METHYL DEC-4-ENOATE | 1.608 | 1.286 |
| 24.03 | 103 | MW168 2-OL? ME 43,81,110,108 | 0.000 | 0.181 |
| 25.18 | 114 | B-FARNESENE | 0.000 | 4.371 |
| 26.10 | 122 | HUMULENE | 1.193 | 14.141 |
| 26.16 | 123 | METHYL DEC-4,8-DIENOATE | 1.462 | 0.310 |
| 26.46 | 129 | WILEY# 123998 MW 204 C15H24 | 0.341 | 0.635 |
| 26.59 | 131 | 2-DODECANONE | 0.311 | 0.000 |
| 27.32 | 138 | A-FARNESENE OR ZINGIBERENE | 0.270 | 0.132 |
| 27.53 | 139 | CAS# 030021-74-0 | 0.000 | 0.000 |
| 27.75 | 143 | A-MUUROLENE | 0.114 | 0.182 |
| 27.90 | 144 | B-SELINENE | 2.421 | 0.109 |
| 28.04 | 145 | A-SELINENE | 2.745 | 0.130 |
| 28.34 | 147 | METHYL ?-UNDECENOATE | 0.266 | 0.308 |
| 29.16 | 154 | D-CADINENE | 0.531 | 0.696 |
| 29.39 | 155 | G-CADINENE | 0.191 | 0.381 |
| 30.34 | 164 | CAS# 016728-99-7 OR G-SELINENE | 3.659 | 0.184 |
| 30.73 | 166 | A-MUUROLINE | 0.000 | 0.000 |
| 31.15 | 170 | 2-TRIDECANONE | 1.620 | 1.080 |
| 31.36 | 171 | GERANYL PROPANOATE | 0.275 | 0.000 |
| 31.46 | 172 | MW 212 METHYL ?-DODECENOATE | 0.000 | 0.000 |
| 32.28 | 177 | trans-GERANIOL | 0.264 | 0.000 |
| 32.54 | 179 | CAS# 000483-77-2 (CALAMENENE ?) | 1.173 | 0.000 |
| 34.38 | 187 | METHYL 3,6-DODECDIENOATE ME 79 | 0.109 | 0.000 |
| 36.42 | 196 | MW 210 ME 43,54,82 | 0.122 | 0.282 |
| 39.11 | 211 | CARYOPHYLLENE OXIDE | 0.121 | 0.083 |
| 40.23 | 221 | HUMULENE MONO-EPOXIDE I | 0.000 | 0.530 |
| 40.28 | 223 | MW222 ME 43,82 | 0.177 | 0.000 |
| 41.07 | 225 | HUMULENE MONO-EPOXIDE II | 0.000 | 0.199 |
| 41.55 | 228 | HUMULENE MONO-EPOXIDE III | 0.000 | 0.000 |
| 41.88 | 231 | MW 222 ME 43,79,80 | 0.598 | 0.950 |
| 43.88 | 242 | MW 220 ME 43,79,91 | 0.170 | 0.262 |
| 44.73 | 246 | T-CADINOL | 0.214 | 0.000 |
| 46.08 | 255 | T-MUUROLOL ME 95,121,204 | 0.000 | 0.000 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 47.50 | 262 | MW 220 ME 41,67,109 DIEPOXIDE? | 0.000 | 0.000 |
| 48.69 | 268 | FARNESOL | 0.407 | 0.000 |

| GC/ FID RT. | CMPD. # | TENTATIVE IDENTIFICATION BY GC/ MASS SPECTROSCOPY | 21080 BACKA | 21287 BANNER |
|---|---|---|---|---|
| 6.42 | 9 | A-PINENE | 0.000 | 0.110 |
| 7.46 | 14 | ISOBUTYL ISOBUTYRATE | 0.000 | 0.129 |
| 8.10 | 16 | 8-PINENE | 0.275 | 0.842 |
| 9.11 | 18 | MYRCENE | 15.376 | 65.305 |
| 9.77 | 22 | 2-METHYL-BUTYL PROPANOATE | 0.075 | 0.391 |
| 9.90 | 23 | ISOAMYL ISOBUTYRATE | 0.000 | 0.173 |
| 9.96 | 24 | 2-METHYL-BUTYL ISOBUTARATE | 0.000 | 0.988 |
| 10.28 | 26 | L-LIMONENE | 0.108 | 0.243 |
| 10.62 | 27 | B-PHELLANDRENE? C10H15 | 0.000 | 0.273 |
| 11.59 | 32 | trans-OCIMENE | 0.000 | 0.681 |
| 12.45 | 35 | 2-METHYL-BUTYL 2-METHYL-BUTYRATE | 0.000 | 0.068 |
| 12.68 | 36 | METHYL HEPTANOATE | 0.281 | 0.381 |
| 12.91 | 40 | ISOAMYL ISOVALERATE | 0.000 | 0.000 |
| 14.31 | 43 | METHYL 4-METHYL-HEXA-2-ENOATE | 0.298 | 0.093 |
| 14.39 | 45 | METHYL 6-METHYL-HEPTANOATE | 0.000 | 0.413 |
| 15.98 | 51 | METHYL OCTANOATE | 0.090 | 0.269 |
| 16.26 | 55 | NONANAL | 0.939 | 0.037 |
| 19.41 | 73 | METHYL NONANOATE | 0.075 | 0.188 |
| 19.56 | 75 | 2-DECANONE, A-YLANGENE | 0.497 | 0.051 |
| 19.93 | 77 | A-COPAENE | 0.420 | 0.173 |
| 21.00 | 83 | LINALOOL | 0.461 | 0.583 |
| 21.31 | 88 | A-GURJUNENE | 0.164 | 0.166 |
| 21.42 | 89 | 7-METHYL-2-DECANONE | 0.384 | 0.000 |
| 22.56 | 93 | C15H24 CALARENE? | 0.382 | 0.069 |
| 22.72 | 95 | A-BERGAMOTENE, METHYL DECANOATE | 0.000 | 0.243 |
| 23.01 | 96 | 2-UNDECANONE | 1.442 | 0.046 |
| 23.10 | 97 | 2-DECANOL | 0.685 | 0.173 |
| 23.44 | 99 | 8-CARYOPHYLLENE | 10.792 | 5.478 |
| 23.84 | 102 | METHYL DEC-4-ENOATE | 0.588 | 0.910 |
| 24.03 | 103 | MW168 2-OL? ME 43,81,110,108 | 0.394 | 0.000 |
| 25.18 | 114 | B-FARNESENE | 0.439 | 0.000 |
| 26.10 | 122 | HUMULENE | 37.338 | 13.256 |
| 26.16 | 123 | METHYL DEC-4,8-DIENOATE | 0.000 | 0.157 |
| 26.46 | 129 | WILEY# 123998 MW 204 C15H24 | 1.342 | 0.475 |
| 26.59 | 131 | 2-DODECANONE | 0.000 | 0.000 |
| 27.32 | 138 | A-FARNESENE OR ZINGIBERENE | 0.114 | 0.134 |
| 27.53 | 139 | CAS# 030021-74-0 | 0.182 | 0.094 |
| 27.75 | 143 | A-MUUROLENE | 0.314 | 0.173 |
| 27.90 | 144 | B-SELINENE | 0.391 | 0.126 |
| 28.04 | 145 | A-SELINENE | 0.429 | 0.140 |
| 28.34 | 147 | METHYL ?-UNDECENOATE | 0.000 | 0.000 |
| 29.16 | 154 | D-CADINENE | 1.688 | 0.873 |
| 29.39 | 155 | G-CADINENE | 1.075 | 0.478 |
| 30.34 | 164 | CAS# 016728-99-7 OR G-SELINENE | 0.263 | 0.126 |
| 30.73 | 166 | A-MUUROLINE | 0.201 | 0.100 |
| 31.15 | 170 | 2-TRIDECANONE | 0.871 | 1.945 |
| 31.36 | 171 | GERANYL PROPANOATE | 0.000 | 0.269 |
| 31.46 | 172 | MW 212 METHYL ?-DODECENOATE | 0.000 | 0.081 |
| 32.28 | 177 | trans-GERANIOL | 0.000 | 0.000 |
| 32.54 | 179 | CAS# 000483-77-2 (CALAMENENE ?) | 0.359 | 0.082 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 34.38 | 187 | METHYL 3,6-DODECDIENOATE ME 79 | 0.000 | 0.484 |
| 36.42 | 196 | MW 210 ME 43,54,82 | 0.236 | 0.137 |
| 39.11 | 211 | CARYOPHYLLENE OXIDE | 2.753 | 0.097 |
| 40.23 | 221 | HUMULENE MONO-EPOXIDE I | 0.173 | 0.048 |
| 40.28 | 223 | MW222 ME 43,82 | 1.201 | 0.113 |
| 41.07 | 225 | HUMULENE MONO-EPOXIDE II | 9.016 | 0.176 |
| 41.55 | 228 | HUMULENE MONO-EPOXIDE III | 0.124 | 0.000 |
| 41.88 | 231 | MW 222 ME 43,79,80 | 1.910 | 0.213 |
| 43.88 | 242 | MW 220 ME 43,79,91 | 0.500 | 0.113 |
| 44.73 | 246 | T-CADINOL | 0.403 | 0.070 |
| 46.08 | 255 | T-MUUROLOL ME 95,121,204 | 0.209 | 0.040 |
| 47.50 | 262 | MW 220 ME 41,67,109 DIEPOXIDE? | 0.333 | 0.000 |
| 48.69 | 268 | FARNESOL | 0.000 | 0.084 |

| GC/ FID RT. | CMPD. # | TENTATIVE IDENTIFICATION BY GC/ MASS SPECTROSCOPY | 21116 BREWERS GOLD | 64100 BULLION |
|---|---|---|---|---|
| 6.42 | 9 | A-PINENE | 0.117 | 0.110 |
| 7.46 | 14 | ISOBUTYL ISOBUTYRATE | 0.169 | 0.251 |
| 8.10 | 16 | 8-PINENE | 0.988 | 0.934 |
| 9.11 | 18 | MYRCENE | 69.050 | 67.113 |
| 9.77 | 22 | 2-METHYL-BUTYL PROPANOATE | 0.344 | 0.469 |
| 9.90 | 23 | ISOAMYL ISOBUTYRATE | 0.068 | 0.153 |
| 9.96 | 24 | 2-METHYL-BUTYL ISOBUTARATE | 1.267 | 1.053 |
| 10.28 | 26 | L-LIMONENE | 0.260 | 0.254 |
| 10.62 | 27 | B-PHELLANDRENE? C10H15 | 0.328 | 0.324 |
| 11.59 | 32 | trans-OCIMENE | 0.549 | 0.441 |
| 12.45 | 35 | 2-METHYL-BUTYL 2-METHYL-BUTYRATE | 0.096 | 0.045 |
| 12.68 | 36 | METHYL HEPTANOATE | 0.298 | 0.543 |
| 12.91 | 40 | ISOAMYL ISOVALERATE | 0.000 | 0.038 |
| 14.31 | 43 | METHYL 4-METHYL-HEXA-2-ENOATE | 0.000 | 0.089 |
| 14.39 | 45 | METHYL 6-METHYL-HEPTANOATE | 0.105 | 0.205 |
| 15.98 | 51 | METHYL OCTANOATE | 0.206 | 0.174 |
| 16.26 | 55 | NONANAL | 0.049 | 0.040 |
| 19.41 | 73 | METHYL NONANOATE | 0.105 | 0.208 |
| 19.56 | 75 | 2-DECANONE, A-YLANGENE | 0.040 | 0.070 |
| 19.93 | 77 | A-COPAENE | 0.166 | 0.149 |
| 21.00 | 83 | LINALOOL | 0.461 | 0.441 |
| 21.31 | 88 | A-GURJUNENE | 0.039 | 0.070 |
| 21.42 | 89 | 7-METHYL-2-DECANONE | 0.000 | 0.000 |
| 22.56 | 93 | C15H24 CALARENE? | 0.085 | 0.064 |
| 22.72 | 95 | A-BERGAMOTENE, METHYL DECANOATE | 0.105 | 0.154 |
| 23.01 | 96 | 2-UNDECANONE | 0.000 | 0.119 |
| 23.10 | 97 | 2-DECANOL | 0.179 | 0.156 |
| 23.44 | 99 | 8-CARYOPHYLLENE | 6.305 | 6.054 |
| 23.84 | 102 | METHYL DEC-4-ENOATE | 0.566 | 0.837 |
| 24.03 | 103 | MW168 2-OL? ME 43,81,110,108 | 0.000 | 0.044 |
| 25.18 | 114 | B-FARNESENE | 0.000 | 0.000 |
| 26.10 | 122 | HUMULENE | 10.326 | 10.525 |
| 26.16 | 123 | METHYL DEC-4,8-DIENOATE | 1.153 | 0.252 |
| 26.46 | 129 | WILEY# 123998 MW 204 C15H24 | 0.433 | 0.396 |
| 26.59 | 131 | 2-DODECANONE | 0.000 | 0.047 |
| 27.32 | 138 | A-FARNESENE OR ZINGIBERENE | 0.177 | 0.169 |
| 27.53 | 139 | CAS# 030021-74-0 | 0.104 | 0.084 |
| 27.75 | 143 | A-MUUROLENE | 0.172 | 0.135 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 27.90 | 144 | B-SELINENE | 0.378 | 0.433 |
| 28.04 | 145 | A-SELINENE | 0.410 | 0.495 |
| 28.34 | 147 | METHYL ?-UNDECENOATE | 0.000 | 0.000 |
| 29.16 | 154 | D-CADINENE | 0.864 | 0.790 |
| 29.39 | 155 | G-CADINENE | 0.443 | 0.387 |
| 30.34 | 164 | CAS# 016728-99-7 OR G-SELINENE | 0.080 | 0.084 |
| 30.73 | 166 | A-MUUROLINE | 0.091 | 0.083 |
| 31.15 | 170 | 2-TRIDECANONE | 0.348 | 0.802 |
| 31.36 | 171 | GERANYL PROPANOATE | 0.257 | 0.493 |
| 31.46 | 172 | MW 212 METHYL ?-DODECENOATE | 0.000 | 0.000 |
| 32.28 | 177 | trans-GERANIOL | 1.003 | 0.060 |
| 32.54 | 179 | CAS# 000483-77-2 (CALAMENENE ?) | 0.000 | 0.051 |
| 34.38 | 187 | METHYL 3,6-DODECDIENOATE ME 79 | 0.000 | 0.126 |
| 36.42 | 196 | MW 210 ME 43,54,82 | 0.000 | 0.267 |
| 39.11 | 211 | CARYOPHYLLENE OXIDE | 0.082 | 0.084 |
| 40.23 | 221 | HUMULENE MONO-EPOXIDE I | 0.097 | 0.227 |
| 40.28 | 223 | MW222 ME 43,82 | 0.047 | 0.107 |
| 41.07 | 225 | HUMULENE MONO-EPOXIDE II | 0.115 | 0.131 |
| 41.55 | 228 | HUMULENE MONO-EPOXIDE III | 0.057 | 0.000 |
| 41.88 | 231 | MW 222 ME 43,79,80 | 0.073 | 0.469 |
| 43.88 | 242 | MW 220 ME 43,79,91 | 0.000 | 0.265 |
| 44.73 | 246 | T-CADINOL | 0.078 | 0.073 |
| 46.08 | 255 | T-MUUROLOL ME 95,121,204 | 0.046 | 0.044 |
| 47.50 | 262 | MW 220 ME 41,67,109 DIEPOXIDE? | 0.000 | 0.000 |
| 48.69 | 268 | FARNESOL | 0.586 | 0.472 |

| GC/ FID RT. | CMPD. # | TENTATIVE IDENTIFICATION BY GC/MASS SPECTROSCOPY | 56013 CASCADE | 21507 CENTENNIAL |
|---|---|---|---|---|
| 6.42 | 9 | A-PINENE | 0.098 | 0.155 |
| 7.46 | 14 | ISOBUTYL ISOBUTYRATE | 0.110 | 0.127 |
| 8.10 | 16 | 8-PINENE | 0.933 | 1.125 |
| 9.11 | 18 | MYRCENE | 68.051 | 77.911 |
| 9.77 | 22 | 2-METHYL-BUTYL PROPANOATE | 0.260 | 0.372 |
| 9.90 | 23 | ISOAMYL ISOBUTYRATE | 0.096 | 0.234 |
| 9.96 | 24 | 2-METHYL-BUTYL ISOBUTARATE | 0.527 | 0.911 |
| 10.28 | 26 | L-LIMONENE | 0.233 | 0.324 |
| 10.62 | 27 | B-PHELLANDRENE? C10H15 | 0.337 | 0.358 |
| 11.59 | 32 | trans-OCIMENE | 0.132 | 0.080 |
| 12.45 | 35 | 2-METHYL-BUTYL 2-METHYL-BUTYRATE | 0.000 | 0.094 |
| 12.68 | 36 | METHYL HEPTANOATE | 0.210 | 0.333 |
| 12.91 | 40 | ISOAMYL ISOVALERATE | 0.043 | 0.126 |
| 14.31 | 43 | METHYL 4-METHYL-HEXA-2-ENOATE | 0.055 | 0.114 |
| 14.39 | 45 | METHYL 6-METHYL-HEPTANOATE | 0.091 | 0.168 |
| 15.98 | 51 | METHYL OCTANOATE | 0.093 | 0.193 |
| 16.26 | 55 | NONANAL | 0.051 | 0.000 |
| 19.41 | 73 | METHYL NONANOATE | 0.072 | 0.101 |
| 19.56 | 75 | 2-DECANONE, A-YLANGENE | 0.044 | 0.000 |
| 19.93 | 77 | A-COPAENE | 0.118 | 0.088 |
| 21.00 | 83 | LINALOOL | 0.312 | 0.470 |
| 21.31 | 88 | A-GURJUNENE | 0.000 | 0.054 |
| 21.42 | 89 | 7-METHYL-2-DECANONE | 0.000 | 0.000 |
| 22.56 | 93 | C15H24 CALARENE? | 0.070 | 0.000 |
| 22.72 | 95 | A-BERGAMOTENE, METHYL DECANOATE | 0.275 | 0.050 |
| 23.01 | 96 | 2-UNDECANONE | 0.110 | 0.000 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 23.10 | 97 | 2-DECANOL | 0.175 | 0.009 |
| 23.44 | 99 | 8-CARYOPHYLLENE | 4.059 | 4.649 |
| 23.84 | 102 | METHYL DEC-4-ENOATE | 0.333 | 0.809 |
| 24.03 | 103 | MW168 2-OL? ME 43,81,110,108 | 0.000 | 0.000 |
| 25.18 | 114 | B-FARNESENE | 5.285 | 0.000 |
| 26.10 | 122 | HUMULENE | 10.063 | 5.699 |
| 26.16 | 123 | METHYL DEC-4,8-DIENOATE | 0.219 | 2.229 |
| 26.46 | 129 | WILEY# 123998 MW 204 C15H24 | 0.325 | 0.239 |
| 26.59 | 131 | 2-DODECANONE | 0.000 | 0.000 |
| 27.32 | 138 | A-FARNESENE OR ZINGIBERENE | 0.311 | 0.110 |
| 27.53 | 139 | CAS# 030021-74-0 | 0.087 | 0.000 |
| 27.75 | 143 | A-MUUROLENE | 0.107 | 0.170 |
| 27.90 | 144 | B-SELINENE | 0.508 | 0.000 |
| 28.04 | 145 | A-SELINENE | 0.533 | 0.050 |
| 28.34 | 147 | METHYL ?-UNDECENOATE | 0.195 | 0.000 |
| 29.16 | 154 | D-CADINENE | 0.624 | 0.420 |
| 29.39 | 155 | G-CADINENE | 0.306 | 0.246 |
| 30.34 | 164 | CAS# 016728-99-7 OR G-SELINENE | 0.071 | 0.000 |
| 30.73 | 166 | A-MUUROLINE | 0.066 | 0.000 |
| 31.15 | 170 | 2-TRIDECANONE | 0.836 | 0.565 |
| 31.36 | 171 | GERANYL PROPANOATE | 0.402 | 0.218 |
| 31.46 | 172 | MW 212 METHYL ?-DODECENOATE | 0.109 | 0.069 |
| 32.28 | 177 | trans-GERANIOL | 0.092 | 0.762 |
| 32.54 | 179 | CAS# 000483-77-2 (CALAMENENE ?) | 0.000 | 0.000 |
| 34.38 | 187 | METHYL 3,6-DODECDIENOATE ME 79 | 0.047 | 0.098 |
| 36.42 | 196 | MW 210 ME 43,54,82 | 0.148 | 0.000 |
| 39.11 | 211 | CARYOPHYLLENE OXIDE | 0.075 | 0.072 |
| 40.23 | 221 | HUMULENE MONO-EPOXIDE I | 0.000 | 0.000 |
| 40.28 | 223 | MW222 ME 43,82 | 0.064 | 0.000 |
| 41.07 | 225 | HUMULENE MONO-EPOXIDE II | 0.157 | 0.114 |
| 41.55 | 228 | HUMULENE MONO-EPOXIDE III | 0.000 | 0.000 |
| 41.88 | 231 | MW 222 ME 43,79,80 | 0.490 | 0.164 |
| 43.88 | 242 | MW 220 ME 43,79,91 | 0.382 | 0.000 |
| 44.73 | 246 | T-CADINOL | 0.069 | 0.000 |
| 46.08 | 255 | T-MUUROLOL ME 95,121,204 | 0.000 | 0.000 |
| 47.50 | 262 | MW 220 ME 41,67,109 DIEPOXIDE? | 0.000 | 0.000 |
| 48.69 | 268 | FARNESOL | 0.093 | 0.000 |

| GC/ FID RT. | CMPD. # | TENTATIVE IDENTIFICATION BY GC/MASS SPECTROSCOPY | 21043 CHALLANGER | 21226 CHINOCK |
|---|---|---|---|---|
| 6.42 | 9 | A-PINENE | 0.078 | 0.102 |
| 7.46 | 14 | ISOBUTYL ISOBUTYRATE | 0.192 | 0.270 |
| 8.10 | 16 | 8-PINENE | 0.765 | 0.768 |
| 9.11 | 18 | MYRCENE | 55.224 | 48.105 |
| 9.77 | 22 | 2-METHYL-BUTYL PROPANOATE | 0.254 | 0.477 |
| 9.90 | 23 | ISOAMYL ISOBUTYRATE | 0.082 | 0.447 |
| 9.96 | 24 | 2-METHYL-BUTYL ISOBUTARATE | 1.164 | 2.385 |
| 10.28 | 26 | L-LIMONENE | 0.204 | 0.210 |
| 10.62 | 27 | B-PHELLANDRENE? C10H15 | 0.260 | 0.228 |
| 11.59 | 32 | trans-OCIMENE | 0.259 | 0.067 |
| 12.45 | 35 | 2-METHYL-BUTYL 2-METHYL-BUTYRATE | 0.067 | 0.185 |
| 12.68 | 36 | METHYL HEPTANOATE | 0.631 | 0.200 |
| 12.91 | 40 | ISOAMYL ISOVALERATE | 0.000 | 0.398 |
| 14.31 | 43 | METHYL 4-METHYL- | 0.337 | 0.099 |

APPENDIX 1-continued

Detailed GLC analysis of assorted hop varieties.
Analytical Conditions: see Kenny (1990), supra.
OIL AREA PERCENTS OF COMMERCIAL HOPS

| GC/ FID RT. | CMPD. # | TENTATIVE IDENTIFICATION BY GC/MASS SPECTROSCOPY | 65103 CLUSTER L-1 | 65103 CLUSTER L-2 |
|---|---|---|---|---|
| | | HEXA-2-ENOATE | | |
| 14.39 | 45 | METHYL 6-METHYL-HEPTANOATE | 0.241 | 1.211 |
| 15.98 | 51 | METHYL OCTANOATE | 0.323 | 0.199 |
| 16.26 | 55 | NONANAL | 0.076 | 0.043 |
| 19.41 | 73 | METHYL NONANOATE | 0.000 | 0.162 |
| 19.56 | 75 | 2-DECANONE, A-YLANGENE | 0.189 | 0.158 |
| 19.93 | 77 | A-COPAENE | 0.164 | 0.530 |
| 21.00 | 83 | LINALOOL | 0.714 | 0.400 |
| 21.31 | 88 | A-GURJUNENE | 0.000 | 0.696 |
| 21.42 | 89 | 7-METHYL-2-DECANONE | 0.076 | 0.079 |
| 22.56 | 93 | C15H24 CALARENE? | 0.109 | 0.186 |
| 22.72 | 95 | A-BERGAMOTENE, METHYL DECANOATE | 0.094 | 0.156 |
| 23.01 | 96 | 2-UNDECANONE | 0.793 | 0.127 |
| 23.10 | 97 | 2-DECANOL | 0.227 | 0.453 |
| 23.44 | 99 | 8-CARYOPHYLLENE | 5.394 | 6.439 |
| 23.84 | 102 | METHYL DEC-4-ENOATE | 0.760 | 1.180 |
| 24.03 | 103 | MW168 2-OL? ME 43,81,110,108 | 0.105 | 0.044 |
| 25.18 | 114 | B-FARNESENE | 1.041 | 0.000 |
| 26.10 | 122 | HUMULENE | 17.304 | 14.547 |
| 26.16 | 123 | METHYL DEC-4,8-DIENOATE | 0.000 | 0.583 |
| 26.46 | 129 | WILEY# 123998 MW 204 C15H24 | 0.232 | 1.511 |
| 26.59 | 131 | 2-DODECANONE | 0.403 | 0.000 |
| 27.32 | 138 | A-FARNESENE OR ZINGIBERENE | 0.319 | 0.362 |
| 27.53 | 139 | CAS# 030021-74-0 | 0.099 | 0.331 |
| 27.75 | 143 | A-MUUROLENE | 0.148 | 0.510 |
| 27.90 | 144 | B-SELINENE | 2.769 | 0.886 |
| 28.04 | 145 | A-SELINENE | 3.204 | 0.971 |
| 28.34 | 147 | METHYL ?-UNDECENOATE | 0.241 | 0.000 |
| 29.16 | 154 | D-CADINENE | 0.810 | 2.685 |
| 29.39 | 155 | G-CADINENE | 0.409 | 1.493 |
| 30.34 | 164 | CAS# 016728-99-7 OR G-SELINENE | 0.105 | 1.965 |
| 30.73 | 166 | A-MUUROLINE | 0.000 | 0.288 |
| 31.15 | 170 | 2-TRIDECANONE | 0.397 | 0.512 |
| 31.36 | 171 | GERANYL PROPANOATE | 0.000 | 0.088 |
| 31.46 | 172 | MW 212 METHYL ?-DODECENOATE | 0.000 | 0.074 |
| 32.28 | 177 | trans-GERANIOL | 0.000 | 0.979 |
| 32.54 | 179 | CAS# 000483-77-2 (CALAMENENE ?) | 0.061 | 0.346 |
| 34.38 | 187 | METHYL 3,6-DODECDIENOATE ME 79 | 0.000 | 0.446 |
| 36.42 | 196 | MW 210 ME 43,54,82 | 0.135 | 0.089 |
| 39.11 | 211 | CARYOPHYLLENE OXIDE | 0.106 | 0.066 |
| 40.23 | 221 | HUMULENE MONO-EPOXIDE I | 0.048 | 0.131 |
| 40.28 | 223 | MW222 ME 43,82 | 0.232 | 0.122 |
| 41.07 | 225 | HUMULENE MONO-EPOXIDE II | 0.250 | 0.153 |
| 41.55 | 228 | HUMULENE MONO-EPOXIDE III | 0.063 | 0.136 |
| 41.88 | 231 | MW 222 ME 43,79,80 | 0.356 | 0.268 |
| 43.88 | 242 | MW 220 ME 43,79,91 | 0.163 | 0.000 |
| 44.73 | 246 | T-CADINOL | 0.077 | 0.248 |
| 46.08 | 255 | T-MUUROLOL ME 95,121,204 | 0.057 | 0.119 |
| 47.50 | 262 | MW 220 ME 41,67,109 DIEPOXIDE? | 0.000 | 0.000 |
| 48.69 | 268 | FARNESOL | 0.076 | 0.524 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 6.42 | 9 | A-PINENE | 0.103 | 0.153 |
| 7.46 | 14 | ISOBUTYL ISOBUTYRATE | 0.280 | 0.153 |
| 8.10 | 16 | 8-PINENE | 0.866 | 0.655 |
| 9.11 | 18 | MYRCENE | 60.712 | 45.653 |
| 9.77 | 22 | 2-METHYL-BUTYL PROPANOATE | 0.536 | 0.335 |
| 9.90 | 23 | ISOAMYL ISOBUTYRATE | 0.483 | 0.525 |
| 9.96 | 24 | 2-METHYL-BUTYL ISOBUTARATE | 1.641 | 1.178 |
| 10.28 | 26 | L-LIMONENE | 0.268 | 0.235 |
| 10.62 | 27 | B-PHELLANDRENE? C10H15 | 0.295 | 0.210 |
| 11.59 | 32 | trans-OCIMENE | 0.370 | 0.229 |
| 12.45 | 35 | 2-METHYL-BUTYL 2-METHYL-BUTYRATE | 0.075 | 0.070 |
| 12.68 | 36 | METHYL HEPTANOATE | 0.244 | 0.220 |
| 12.91 | 40 | ISOAMYL ISOVALERATE | 0.187 | 0.271 |
| 14.31 | 43 | METHYL 4-METHYL-HEXA-2-ENOATE | 0.342 | 0.310 |
| 14.39 | 45 | METHYL 6-METHYL-HEPTANOATE | 0.447 | 0.399 |
| 15.98 | 51 | METHYL OCTANOATE | 0.721 | 0.555 |
| 16.26 | 55 | NONANAL | 0.250 | 0.467 |
| 19.41 | 73 | METHYL NONANOATE | 0.165 | 0.158 |
| 19.56 | 75 | 2-DECANONE, A-YLANGENE | 0.060 | 0.100 |
| 19.93 | 77 | A-COPAENE | 0.126 | 0.242 |
| 21.00 | 83 | LINALOOL | 0.347 | 0.259 |
| 21.31 | 88 | A-GURJUNENE | 0.372 | 0.374 |
| 21.42 | 89 | 7-METHYL-2-DECANONE | 0.071 | 0.075 |
| 22.56 | 93 | C15H24 CALARENE? | 0.082 | 0.158 |
| 22.72 | 95 | A-BERGAMOTENE, METHYL DECANOATE | 0.953 | 0.855 |
| 23.01 | 96 | 2-UNDECANONE | 0.533 | 0.648 |
| 23.10 | 97 | 2-DECANOL | 0.180 | 0.352 |
| 23.44 | 99 | 8-CARYOPHYLLENE | 4.725 | 8.080 |
| 23.84 | 102 | METHYL DEC-4-ENOATE | 1.801 | 1.927 |
| 24.03 | 103 | MW168 2-OL? ME 43,81,110,108 | 0.073 | 0.108 |
| 25.18 | 114 | B-FARNESENE | 0.000 | 0.000 |
| 26.10 | 122 | HUMULENE | 13.195 | 20.805 |
| 26.16 | 123 | METHYL DEC-4,8-DIENOATE | 0.154 | 0.132 |
| 26.46 | 129 | WILEY# 123998 MW 204 C15H24 | 0.306 | 0.538 |
| 26.59 | 131 | 2-DODECANONE | 0.064 | 0.078 |
| 27.32 | 138 | A-FARNESENE OR ZINGIBERENE | 0.135 | 0.197 |
| 27.53 | 139 | CAS# 030021-74-0 | 0.084 | 0.137 |
| 27.75 | 143 | A-MUUROLENE | 0.127 | 0.216 |
| 27.90 | 144 | B-SELINENE | 0.319 | 0.558 |
| 28.04 | 145 | A-SELINENE | 0.356 | 0.612 |
| 28.34 | 147 | METHYL ?-UNDECENOATE | 0.000 | 0.000 |
| 29.16 | 154 | D-CADINENE | 0.655 | 1.137 |
| 29.39 | 155 | G-CADINENE | 0.330 | 0.604 |
| 30.34 | 164 | CAS# 016728-99-7 OR G-SELINENE | 0.081 | 0.141 |
| 30.73 | 166 | A-MUUROLINE | 0.059 | 0.110 |
| 31.15 | 170 | 2-TRIDECANONE | 0.843 | 1.060 |
| 31.36 | 171 | GERANYL PROPANOATE | 0.000 | 0.000 |
| 31.46 | 172 | MW 212 METHYL ?-DODECENOATE | 0.741 | 0.925 |
| 32.28 | 177 | trans-GERANIOL | 0.703 | 0.446 |
| 32.54 | 179 | CAS# 000483-77-2 (CALAMENENE ?) | 0.000 | 0.108 |
| 34.38 | 187 | METHYL 3,6-DODECDIENOATE ME 79 | 0.228 | 0.221 |
| 36.42 | 196 | MW 210 ME 43,54,82 | 0.062 | 0.082 |
| 39.11 | 211 | CARYOPHYLLENE OXIDE | 0.094 | 0.251 |
| 40.23 | 221 | HUMULENE MONO-EPOXIDE I | 0.000 | 0.147 |
| 40.28 | 223 | MW222 ME 43,82 | 0.151 | 0.201 |
| 41.07 | 225 | HUMULENE MONO-EPOXIDE II | 0.237 | 0.653 |
| 41.55 | 228 | HUMULENE | 0.000 | 0.137 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| | | MONO-EPOXIDE III | | |
| 41.88 | 231 | MW 222 ME 43,79,80 | 0.666 | 1.036 |
| 43.88 | 242 | MW 220 ME 43,79,91 | 0.429 | 0.609 |
| 44.73 | 246 | T-CADINOL | 0.088 | 0.170 |
| 46.08 | 255 | T-MUUROLOL ME 95,121,204 | 0.000 | 0.090 |
| 47.50 | 262 | MW 220 ME 41,67,109 DIEPOXIDE? | 0.000 | 0.077 |
| 48.69 | 268 | FARNESOL | 0.066 | 0.084 |

| GC/ FID RT. | CMPD. # | TENTATIVE IDENTIFICATION BY GC/ MASS SPECTROSCOPY | 21220 EROICA | 21016 FUGGLE |
|---|---|---|---|---|
| 6.42 | 9 | A-PINENE | 0.155 | 0.075 |
| 7.46 | 14 | ISOBUTYL ISOBUTYRATE | 0.000 | 0.221 |
| 8.10 | 16 | 8-PINENE | 0.884 | 0.712 |
| 9.11 | 18 | MYRCENE | 61.773 | 54.039 |
| 9.77 | 22 | 2-METHYL-BUTYL PROPANOATE | 0.237 | 0.157 |
| 9.90 | 23 | ISOAMYL ISOBUTYRATE | 0.124 | 0.000 |
| 9.96 | 24 | 2-METHYL-BUTYL ISOBUTARATE | 0.549 | 0.443 |
| 10.28 | 26 | L-LIMONENE | 0.233 | 0.186 |
| 10.62 | 27 | B-PHELLANDRENE? C10H15 | 0.264 | 0.242 |
| 11.59 | 32 | trans-OCIMENE | 1.577 | 0.105 |
| 12.45 | 35 | 2-METHYL-BUTYL 2-METHYL-BUTYRATE | 0.000 | 0.000 |
| 12.68 | 36 | METHYL HEPTANOATE | 0.292 | 0.426 |
| 12.91 | 40 | ISOAMYL ISOVALERATE | 0.000 | 0.000 |
| 14.31 | 43 | METHYL 4-METHYL-HEXA-2-ENOATE | 0.000 | 0.170 |
| 14.39 | 45 | METHYL 6-METHYL-HEPTANOATE | 0.271 | 0.114 |
| 15.98 | 51 | METHYL OCTANOATE | 0.257 | 0.088 |
| 16.26 | 55 | NONANAL | 0.070 | 0.098 |
| 19.41 | 73 | METHYL NONANOATE | 0.204 | 0.097 |
| 19.56 | 75 | 2-DECANONE, A-YLANGENE | 0.161 | 0.212 |
| 19.93 | 77 | A-COPAENE | 0.053 | 0.225 |
| 21.00 | 83 | LINALOOL | 0.508 | 0.651 |
| 21.31 | 88 | A-GURJUNENE | 0.155 | 0.000 |
| 21.42 | 89 | 7-METHYL-2-DECANONE | 0.214 | 0.083 |
| 22.56 | 93 | C15H24 CALARENE? | 0.000 | 0.157 |
| 22.72 | 95 | A-BERGAMOTENE, METHYL DECANOATE | 0.325 | 0.272 |
| 23.01 | 96 | 2-UNDECANONE | 0.820 | 0.406 |
| 23.10 | 97 | 2-DECANOL | 0.000 | 0.348 |
| 23.44 | 99 | 8-CARYOPHYLLENE | 12.756 | 7.628 |
| 23.84 | 102 | METHYL DEC-4-ENOATE | 0.875 | 0.409 |
| 24.03 | 103 | MW168 2-OL? ME 43,81,110,108 | 0.167 | 0.122 |
| 25.18 | 114 | B-FARNESENE | 0.000 | 4.870 |
| 26.10 | 122 | HUMULENE | 0.355 | 20.059 |
| 26.16 | 123 | METHYL DEC-4,8-DIENOATE | 0.419 | 0.147 |
| 26.46 | 129 | WILEY# 123998 MW 204 C15H24 | 0.104 | 0.528 |
| 26.59 | 131 | 2-DODECANONE | 0.344 | 0.073 |
| 27.32 | 138 | A-FARNESENE OR ZINGIBERENE | 0.000 | 0.543 |
| 27.53 | 139 | CAS# 030021-74-0 | 0.000 | 0.090 |
| 27.75 | 143 | A-MUUROLENE | 0.060 | 0.173 |
| 27.90 | 144 | B-SELINENE | 2.268 | 0.177 |
| 28.04 | 145 | A-SELINENE | 2.562 | 0.186 |
| 28.34 | 147 | METHYL ?-UNDECENOATE | 0.000 | 0.424 |
| 29.16 | 154 | D-CADINENE | 0.293 | 1.092 |
| 29.39 | 155 | G-CADINENE | 0.167 | 0.573 |
| 30.34 | 164 | CAS# 016728-99-7 OR G-SELINENE | 0.000 | 0.147 |
| 30.73 | 166 | A-MUUROLINE | 0.000 | 0.117 |
| 31.15 | 170 | 2-TRIDECANONE | 0.606 | 0.397 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 31.36 | 171 | GERANYL PROPANOATE | 0.091 | 0.000 |
| 31.46 | 172 | MW 212 METHYL ?-DODECENOATE | 0.000 | 0.000 |
| 32.28 | 177 | trans-GERANIOL | 0.949 | 0.000 |
| 32.54 | 179 | CAS# 000483-77-2 (CALAMENENE ?) | 0.077 | 0.080 |
| 34.38 | 187 | METHYL 3,6-DODECDIENOATE ME 79 | 0.228 | 0.064 |
| 36.42 | 196 | MW 210 ME 43,54,82 | 0.437 | 0.080 |
| 39.11 | 211 | CARYOPHYLLENE OXIDE | 0.156 | 0.126 |
| 40.23 | 221 | HUMULENE MONO-EPOXIDE I | 0.164 | 0.000 |
| 40.28 | 223 | MW222 ME 43,82 | 0.878 | 0.087 |
| 41.07 | 225 | HUMULENE MONO-EPOXIDE II | 0.000 | 0.279 |
| 41.55 | 228 | HUMULENE MONO-EPOXIDE III | 0.000 | 0.088 |
| 41.88 | 231 | MW 222 ME 43,79,80 | 1.761 | 0.435 |
| 43.88 | 242 | MW 220 ME 43,79,91 | 0.461 | 0.235 |
| 44.73 | 246 | T-CADINOL | 0.055 | 0.125 |
| 46.08 | 255 | T-MUUROLOL ME 95,121,204 | 0.000 | 0.070 |
| 47.50 | 262 | MW 220 ME 41,67,109 DIEPOXIDE? | 0.000 | 0.000 |
| 48.69 | 268 | FARNESOL | 0.326 | 0.134 |

| GC/ FID RT. | CMPD. # | TENTATIVE IDENTIFICATION BY GC/ MASS SPECTROSCOPY | 21102 GALENA | 21014 HALLERTAU |
|---|---|---|---|---|
| 6.42 | 9 | A-PINENE | 0.109 | 0.064 |
| 7.46 | 14 | ISOBUTYL ISOBUTYRATE | 0.479 | 0.151 |
| 8.10 | 16 | 8-PINENE | 0.027 | 0.653 |
| 9.11 | 18 | MYRCENE | 55.179 | 53.508 |
| 9.77 | 22 | 2-METHYL-BUTYL PROPANOATE | 1.009 | 0.184 |
| 9.90 | 23 | ISOAMYL ISOBUTYRATE | 0.554 | 0.000 |
| 9.96 | 24 | 2-METHYL-BUTYL ISOBUTARATE | 5.004 | 0.278 |
| 10.28 | 26 | L-LIMONENE | 0.218 | 0.158 |
| 10.62 | 27 | B-PHELLANDRENE? C10H15 | 0.239 | 0.204 |
| 11.59 | 32 | trans-OCIMENE | 2.260 | 0.144 |
| 12.45 | 35 | 2-METHYL-BUTYL 2-METHYL-BUTYRATE | 0.151 | 0.000 |
| 12.68 | 36 | METHYL HEPTANOATE | 0.427 | 0.647 |
| 12.91 | 40 | ISOAMYL ISOVALERATE | 0.169 | 0.000 |
| 14.31 | 43 | METHYL 4-METHYL-HEXA-2-ENOATE | 0.152 | 0.264 |
| 14.39 | 45 | METHYL 6-METHYL-HEPTANOATE | 0.930 | 0.150 |
| 15.98 | 51 | METHYL OCTANOATE | 0.878 | 0.203 |
| 16.26 | 55 | NONANAL | 0.079 | 0.095 |
| 19.41 | 73 | METHYL NONANOATE | 0.436 | 0.138 |
| 19.56 | 75 | 2-DECANONE, A-YLANGENE | 0.071 | 0.258 |
| 19.93 | 77 | A-COPAENE | 0.111 | 0.214 |
| 21.00 | 83 | LINALOOL | 0.206 | 0.939 |
| 21.31 | 88 | A-GURJUNENE | 0.577 | 0.044 |
| 21.42 | 89 | 7-METHYL-2-DECANONE | 0.009 | 0.086 |
| 22.56 | 93 | C15H24 CALARENE? | 0.053 | 0.120 |
| 22.72 | 95 | A-BERGAMOTENE, METHYL DECANOATE | 1.317 | 0.000 |
| 23.01 | 96 | 2-UNDECANONE | 0.386 | 0.696 |
| 23.10 | 97 | 2-DECANOL | 0.131 | 0.337 |
| 23.44 | 99 | 8-CARYOPHYLLENE | 4.602 | 7.238 |
| 23.84 | 102 | METHYL DEC-4-ENOATE | 2.237 | 0.660 |
| 24.03 | 103 | MW168 2-OL? ME 43,81,110,108 | 0.042 | 0.157 |
| 25.18 | 114 | B-FARNESENE | 0.000 | 0.000 |
| 26.10 | 122 | HUMULENE | 10.599 | 24.799 |
| 26.16 | 123 | METHYL DEC-4,8-DIENOATE | 0.180 | 0.000 |
| 26.46 | 129 | WILEY# 123998 MW 204 | 0.281 | 0.670 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| | | C15H24 | | |
| 26.59 | 131 | 2-DODECANONE | 0.076 | 0.132 |
| 27.32 | 138 | A-FARNESENE OR ZINGIBERENE | 0.000 | 0.227 |
| 27.53 | 139 | CAS# 030021-74-0 | 0.054 | 0.113 |
| 27.75 | 143 | A-MUUROLENE | 0.101 | 0.214 |
| 27.90 | 144 | B-SELINENE | 0.465 | 0.190 |
| 28.04 | 145 | A-SELINENE | 0.544 | 0.207 |
| 28.34 | 147 | METHYL ?-UNDECENOATE | 0.000 | 0.069 |
| 29.16 | 154 | D-CADINENE | 0.586 | 1.250 |
| 29.39 | 155 | G-CADINENE | 0.300 | 0.653 |
| 30.34 | 164 | CAS# 016728-99-7 OR G-SELINENE | 0.142 | 0.151 |
| 30.73 | 166 | A-MUUROLINE | 0.064 | 0.136 |
| 31.15 | 170 | 2-TRIDECANONE | 1.561 | 0.421 |
| 31.36 | 171 | GERANYL PROPANOATE | 0.119 | 0.000 |
| 31.46 | 172 | MW 212 METHYL ?-DODECENOATE | 0.219 | 0.000 |
| 32.28 | 177 | trans-GERANIOL | 0.000 | 0.000 |
| 32.54 | 179 | CAS# 000483-77-2 (CALAMENENE ?) | 0.000 | 0.102 |
| 34.38 | 187 | METHYL 3,6-DODECDIENOATE ME 79 | 1.725 | 0.071 |
| 36.42 | 196 | MW 210 ME 43,54,82 | 0.186 | 0.125 |
| 39.11 | 211 | CARYOPHYLLENE OXIDE | 0.064 | 0.111 |
| 40.23 | 221 | HUMULENE MONO-EPOXIDE I | 0.000 | 0.099 |
| 40.28 | 223 | MW222 ME 43,82 | 0.237 | 0.239 |
| 41.07 | 225 | HUMULENE MONO-EPOXIDE II | 0.134 | 0.357 |
| 41.55 | 228 | HUMULENE MONO-EPOXIDE III | 0.000 | 0.100 |
| 41.88 | 231 | MW 222 ME 43,79,80 | 0.579 | 0.638 |
| 43.88 | 242 | MW 220 ME 43,79,91 | 0.263 | 0.263 |
| 44.73 | 246 | T-CADINOL | 0.059 | 0.125 |
| 46.08 | 255 | T-MUUROLOL ME 95,121,204 | 0.000 | 0.075 |
| 47.50 | 262 | MW 220 ME 41,67,109 DIEPOXIDE? | 0.000 | 0.000 |
| 48.69 | 268 | FARNESOL | 0.000 | 0.064 |

| GC/ FID RT. | CMPD. # | TENTATIVE IDENTIFICATION BY GC/ MASS SPECTROSCOPY | 21135 HERSBRUCK | 21097 HULLERER BITTERER |
|---|---|---|---|---|
| 6.42 | 9 | A-PINENE | 0.000 | 0.087 |
| 7.46 | 14 | ISOBUTYL ISOBUTYRATE | 0.000 | 0.088 |
| 8.10 | 16 | 8-PINENE | 0.527 | 0.737 |
| 9.11 | 18 | MYRCENE | 44.828 | 52.818 |
| 9.77 | 22 | 2-METHYL-BUTYL PROPANOATE | 0.000 | 0.415 |
| 9.90 | 23 | ISOAMYL ISOBUTYRATE | 0.000 | 0.168 |
| 9.96 | 24 | 2-METHYL-BUTYL ISOBUTARATE | 0.066 | 0.844 |
| 10.28 | 26 | L-LIMONENE | 0.147 | 0.207 |
| 10.62 | 27 | B-PHELLANDRENE? C10H15 | 0.145 | 0.212 |
| 11.59 | 32 | trans-OCIMENE | 0.000 | 0.092 |
| 12.45 | 35 | 2-METHYL-BUTYL 2-METHYL-BUTYRATE | 0.000 | 0.079 |
| 12.68 | 36 | METHYL HEPTANOATE | 0.418 | 0.231 |
| 12.91 | 40 | ISOAMYL ISOVALERATE | 0.000 | 0.075 |
| 14.31 | 43 | METHYL 4-METHYL-HEXA-2-ENOATE | 0.289 | 0.000 |
| 14.39 | 45 | METHYL 6-METHYL-HEPTANOATE | 0.171 | 0.408 |
| 15.98 | 51 | METHYL OCTANOATE | 0.134 | 0.110 |
| 16.26 | 55 | NONANAL | 0.226 | 0.084 |
| 19.41 | 73 | METHYL NONANOATE | 0.090 | 0.088 |
| 19.56 | 75 | 2-DECANONE, A-YLANGENE | 0.334 | 0.251 |
| 19.93 | 77 | A-COPAENE | 0.259 | 0.617 |
| 21.00 | 83 | LINALOOL | 0.805 | 0.503 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 21.31 | 88 | A-GURJUNENE | 0.077 | 0.169 |
| 21.42 | 89 | 7-METHYL-2-DECANONE | 0.214 | 0.121 |
| 22.56 | 93 | C15H24 CALARENE? | 0.190 | 0.300 |
| 22.72 | 95 | A-BERGAMOTENE, METHYL DECANOATE | 0.000 | 0.000 |
| 23.01 | 96 | 2-UNDECANONE | 0.921 | 0.387 |
| 23.10 | 97 | 2-DECANOL | 0.531 | 0.602 |
| 23.44 | 99 | 8-CARYOPHYLLENE | 5.573 | 4.386 |
| 23.84 | 102 | METHYL DEC-4-ENOATE | 0.551 | 0.772 |
| 24.03 | 103 | MW168 2-OL? ME 43,81,110,108 | 0.210 | 0.122 |
| 25.18 | 114 | B-FARNESENE | 0.324 | 0.093 |
| 26.10 | 122 | HUMULENE | 29.352 | 8.090 |
| 26.16 | 123 | METHYL DEC-4,8-DIENOATE | 0.132 | 0.352 |
| 26.46 | 129 | WILEY# 123998 MW 204 C15H24 | 0.735 | 1.994 |
| 26.59 | 131 | 2-DODECANONE | 0.203 | 0.000 |
| 27.32 | 138 | A-FARNESENE OR ZINGIBERENE | 0.326 | 0.273 |
| 27.53 | 139 | CAS# 030021-74-0 | 0.103 | 0.352 |
| 27.75 | 143 | A-MUUROLENE | 0.248 | 0.574 |
| 27.90 | 144 | B-SELINENE | 0.306 | 2.221 |
| 28.04 | 145 | A-SELINENE | 0.335 | 2.426 |
| 28.34 | 147 | METHYL ?-UNDECENOATE | 0.191 | 0.399 |
| 29.16 | 154 | D-CADINENE | 1.330 | 2.714 |
| 29.39 | 155 | G-CADINENE | 0.746 | 1.516 |
| 30.34 | 164 | CAS# 016728-99-7 OR G-SELINENE | 0.141 | 3.993 |
| 30.73 | 166 | A-MUUROLINE | 0.146 | 0.364 |
| 31.15 | 170 | 2-TRIDECANONE | 0.580 | 0.241 |
| 31.36 | 171 | GERANYL PROPANOATE | 0.000 | 0.000 |
| 31.46 | 172 | MW 212 METHYL ?-DODECENOATE | 0.000 | 0.000 |
| 32.28 | 177 | trans-GERANIOL | 0.000 | 0.134 |
| 32.54 | 179 | CAS# 000483-77-2 (CALAMENENE ?) | 0.229 | 0.205 |
| 34.38 | 187 | METHYL 3,6-DODECDIENOATE ME 79 | 0.000 | 0.340 |
| 36.42 | 196 | MW 210 ME 43,54,82 | 0.147 | 0.179 |
| 39.11 | 211 | CARYOPHYLLENE OXIDE | 0.331 | 0.082 |
| 40.23 | 221 | HUMULENE MONO-EPOXIDE I | 0.145 | 0.137 |
| 40.28 | 223 | MW222 ME 43,82 | 0.260 | 0.000 |
| 41.07 | 225 | HUMULENE MONO-EPOXIDE II | 0.962 | 0.194 |
| 41.55 | 228 | HUMULENE MONO-EPOXIDE III | 0.159 | 0.074 |
| 41.88 | 231 | MW 222 ME 43,79,80 | 0.752 | 0.531 |
| 43.88 | 242 | MW 220 ME 43,79,91 | 0.489 | 0.195 |
| 44.73 | 246 | T-CADINOL | 0.177 | 0.336 |
| 46.08 | 255 | T-MUUROLOL ME 95,121,204 | 0.114 | 0.132 |
| 47.50 | 262 | MW 220 ME 41,67,109 DIEPOXIDE? | 0.000 | 0.000 |
| 48.69 | 268 | FARNESOL | 0.161 | 0.166 |

| GC/ FID RT. | CMPD. # | TENTATIVE IDENTIFICATION BY GC/ MASS SPECTROSCOPY | 21457 LIBERTY | 21113 LUBELSKA |
|---|---|---|---|---|
| 6.42 | 9 | A-PINENE | 0.043 | 0.047 |
| 7.46 | 14 | ISOBUTYL ISOBUTYRATE | 0.068 | 0.000 |
| 8.10 | 16 | 8-PINENE | 0.504 | 0.421 |
| 9.11 | 18 | MYRCENE | 41.506 | 29.558 |
| 9.77 | 22 | 2-METHYL-BUTYL PROPANOATE | 0.117 | 0.000 |
| 9.90 | 23 | ISOAMYL ISOBUTYRATE | 0.000 | 0.000 |
| 9.96 | 24 | 2-METHYL-BUTYL ISOBUTARATE | 0.197 | 0.176 |
| 10.28 | 26 | L-LIMONENE | 0.124 | 0.145 |
| 10.62 | 27 | B-PHELLANDRENE? C10H15 | 0.149 | 0.099 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 11.59 | 32 | trans-OCIMENE | 0.066 | 0.000 |
| 12.45 | 35 | 2-METHYL-BUTYL 2-METHYL-BUTYRATE | 0.000 | 0.000 |
| 12.68 | 36 | METHYL HEPTANOATE | 0.293 | 0.259 |
| 12.91 | 40 | ISOAMYL ISOVALERATE | 0.000 | 0.000 |
| 14.31 | 43 | METHYL 4-METHYL-HEXA-2-ENOATE | 0.128 | 0.081 |
| 14.39 | 45 | METHYL 6-METHYL-HEPTANOATE | 0.083 | 0.148 |
| 15.98 | 51 | METHYL OCTANOATE | 0.189 | 0.100 |
| 16.26 | 55 | NONANAL | 0.091 | 0.193 |
| 19.41 | 73 | METHYL NONANOATE | 0.092 | 0.183 |
| 19.56 | 75 | 2-DECANONE, A-YLANGENE | 0.240 | 0.268 |
| 19.93 | 77 | A-COPAENE | 0.304 | 0.268 |
| 21.00 | 83 | LINALOOL | 0.814 | 0.254 |
| 21.31 | 88 | A-GURJUNENE | 0.043 | 0.106 |
| 21.42 | 89 | 7-METHYL-2-DECANONE | 0.098 | 0.198 |
| 22.56 | 93 | C15H24 CALARENE? | 0.172 | 0.179 |
| 22.72 | 95 | A-BERGAMOTENE, METHYL DECANOATE | 0.000 | 0.947 |
| 23.01 | 96 | 2-UNDECANONE | 0.737 | 0.690 |
| 23.10 | 97 | 2-DECANOL | 0.442 | 0.443 |
| 23.44 | 99 | 8-CARYOPHYLLENE | 9.651 | 6.953 |
| 23.84 | 102 | METHYL DEC-4-ENOATE | 0.663 | 1.089 |
| 24.03 | 103 | MW168 2-OL? ME 43,81,110,108 | 0.140 | 0.207 |
| 25.18 | 114 | B-FARNESENE | 0.080 | 17.712 |
| 26.10 | 122 | HUMULENE | 32.402 | 21.404 |
| 26.16 | 123 | METHYL DEC-4,8-DIENOATE | 0.075 | 0.451 |
| 26.46 | 129 | WILEY# 123998 MW 204 C15H24 | 0.387 | 0.796 |
| 26.59 | 131 | 2-DODECANONE | 0.105 | 0.167 |
| 27.32 | 138 | A-FARNESENE OR ZINGIBERENE | 0.509 | 0.316 |
| 27.53 | 139 | CAS# 030021-74-0 | 0.181 | 0.157 |
| 27.75 | 143 | A-MUUROLENE | 0.289 | 0.282 |
| 27.90 | 144 | B-SELINENE | 0.325 | 1.492 |
| 28.04 | 145 | A-SELINENE | 0.358 | 1.546 |
| 28.34 | 147 | METHYL ?-UNDECENOATE | 0.310 | 0.242 |
| 29.16 | 154 | D-CADINENE | 1.508 | 1.438 |
| 29.39 | 155 | G-CADINENE | 0.887 | 0.811 |
| 30.34 | 164 | CAS# 016728-99-7 OR G-SELINENE | 0.213 | 0.237 |
| 30.73 | 166 | A-MUUROLINE | 0.103 | 0.159 |
| 31.15 | 170 | 2-TRIDECANONE | 0.458 | 0.738 |
| 31.36 | 171 | GERANYL PROPANOATE | 0.000 | 0.000 |
| 31.46 | 172 | MW 212 METHYL ?-DODECENOATE | 0.000 | 0.070 |
| 32.28 | 177 | trans-GERANIOL | 0.099 | 0.257 |
| 32.54 | 179 | CAS# 000483-77-2 (CALAMENENE ?) | 0.193 | 0.196 |
| 34.38 | 187 | METHYL 3,6-DODECDIENOATE ME 79 | 0.057 | 0.203 |
| 36.42 | 196 | MW 210 ME 43,54,82 | 0.115 | 0.199 |
| 39.11 | 211 | CARYOPHYLLENE OXIDE | 0.205 | 0.550 |
| 40.23 | 221 | HUMULENE MONO-EPOXIDE I | 0.103 | 0.298 |
| 40.28 | 223 | MW222 ME 43,82 | 0.308 | 0.261 |
| 41.07 | 225 | HUMULENE MONO-EPOXIDE II | 0.599 | 1.612 |
| 41.55 | 228 | HUMULENE MONO-EPOXIDE III | 0.144 | 0.000 |
| 41.88 | 231 | MW 222 ME 43,79,80 | 0.568 | 1.358 |
| 43.88 | 242 | MW 220 ME 43,79,91 | 0.342 | 0.439 |
| 44.73 | 246 | T-CADINOL | 0.179 | 0.247 |
| 46.08 | 255 | T-MUUROLOL ME 95,121,204 | 0.128 | 0.131 |
| 47.50 | 262 | MW 220 ME 41,67,109 DIEPOXIDE? | 0.000 | 0.094 |
| 48.69 | 268 | FARNESOL | 0.340 | 0.339 |

APPENDIX 1-continued

Detailed GLC analysis of assorted hop varieties.
Analytical Conditions: see Kenny (1990), supra.
OIL AREA PERCENTS OF COMMERCIAL HOPS

| GC/ FID RT. | CMPD. # | TENTATIVE IDENTIFICATION BY GC/ MASS SPECTROSCOPY | 21114 NADWIS-LANSKA | 21073 NORTH-ERN BREWER |
|---|---|---|---|---|
| 6.42 | 9 | A-PINENE | 0.066 | 0.125 |
| 7.46 | 14 | ISOBUTYL ISOBUTYRATE | 0.000 | 0.174 |
| 8.10 | 16 | 8-PINENE | 0.649 | 0.862 |
| 9.11 | 18 | MYRCENE | 44.179 | 55.587 |
| 9.77 | 22 | 2-METHYL-BUTYL PROPANOATE | 0.000 | 0.183 |
| 9.90 | 23 | ISOAMYL ISOBUTYRATE | 0.000 | 0.108 |
| 9.96 | 24 | 2-METHYL-BUTYL ISOBUTARATE | 0.000 | 0.428 |
| 10.28 | 26 | L-LIMONENE | 0.169 | 0.248 |
| 10.62 | 27 | B-PHELLANDRENE? C10H15 | 0.149 | 0.265 |
| 11.59 | 32 | trans-OCIMENE | 0.000 | 0.488 |
| 12.45 | 35 | 2-METHYL-BUTYL 2-METHYL-BUTYRATE | 0.000 | 0.000 |
| 12.68 | 36 | METHYL HEPTANOATE | 0.391 | 0.706 |
| 12.91 | 40 | ISOAMYL ISOVALERATE | 0.000 | 0.000 |
| 14.31 | 43 | METHYL 4-METHYL-HEXA-2-ENOATE | 0.206 | 0.251 |
| 14.39 | 45 | METHYL 6-METHYL-HEPTANOATE | 0.178 | 0.150 |
| 15.98 | 51 | METHYL OCTANOATE | 0.113 | 0.199 |
| 16.26 | 55 | NONANAL | 0.141 | 0.077 |
| 19.41 | 73 | METHYL NONANOATE | 0.155 | 0.166 |
| 19.56 | 75 | 2-DECANONE, A-YLANGENE | 0.260 | 0.177 |
| 19.93 | 77 | A-COPAENE | 0.160 | 0.284 |
| 21.00 | 83 | LINALOOL | 0.390 | 0.344 |
| 21.31 | 88 | A-GURJUNENE | 0.073 | 0.000 |
| 21.42 | 89 | 7-METHYL-2-DECANONE | 0.116 | 0.049 |
| 22.56 | 93 | C15H24 CALARENE? | 0.113 | 0.154 |
| 22.72 | 95 | A-BERGAMOTENE, METHYL DECANOATE | 0.854 | 0.000 |
| 23.01 | 96 | 2-UNDECANONE | 0.592 | 0.292 |
| 23.10 | 97 | 2-DECANOL | 0.284 | 0.307 |
| 23.44 | 99 | 8-CARYOPHYLLENE | 5.415 | 9.217 |
| 23.84 | 102 | METHYL DEC-4-ENOATE | 0.939 | 0.565 |
| 24.03 | 103 | MW168 2-OL? ME 43,81,110,108 | 0.211 | 0.077 |
| 25.18 | 114 | B-FARNESENE | 17.417 | 0.000 |
| 26.10 | 122 | HUMULENE | 18.740 | 21.642 |
| 26.16 | 123 | METHYL DEC-4,8-DIENOATE | 0.368 | 0.389 |
| 26.46 | 129 | WILEY# 123998 MW 204 C15H24 | 0.461 | 0.619 |
| 26.59 | 131 | 2-DODECANONE | 0.127 | 0.084 |
| 27.32 | 138 | A-FARNESENE OR ZINGIBERENE | 0.264 | 0.179 |
| 27.53 | 139 | CAS# 030021-74-0 | 0.053 | 0.112 |
| 27.75 | 143 | A-MUUROLENE | 0.143 | 0.217 |
| 27.90 | 144 | B-SELINENE | 0.217 | 0.182 |
| 28.04 | 145 | A-SELINENE | 0.161 | 0.210 |
| 28.34 | 147 | METHYL ?-UNDECENOATE | 0.206 | 0.000 |
| 29.16 | 154 | D-CADINENE | 0.766 | 1.301 |
| 29.39 | 155 | G-CADINENE | 0.431 | 0.650 |
| 30.34 | 164 | CAS# 016728-99-7 OR G-SELINENE | 0.121 | 0.129 |
| 30.73 | 166 | A-MUUROLINE | 0.085 | 0.124 |
| 31.15 | 170 | 2-TRIDECANONE | 0.417 | 0.337 |
| 31.36 | 171 | GERANYL PROPANOATE | 0.000 | 0.000 |
| 31.46 | 172 | MW 212 METHYL ?-DODECENOATE | 0.000 | 0.000 |
| 32.28 | 177 | trans-GERANIOL | 0.200 | 0.000 |
| 32.54 | 179 | CAS# 000483-77-2 (CALAMENENE ?) | 0.131 | 0.110 |
| 34.38 | 187 | METHYL 3,6-DODECDIENOATE ME 79 | 0.146 | 0.068 |
| 36.42 | 196 | MW 210 ME 43,54,82 | 0.127 | 0.082 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 39.11 | 211 | CARYOPHYLLENE OXIDE | 0.284 | 0.122 |
| 40.23 | 221 | HUMULENE MONO-EPOXIDE I | 0.156 | 0.065 |
| 40.28 | 223 | MW222 ME 43,82 | 0.127 | 0.109 |
| 41.07 | 225 | HUMULENE MONO-EPOXIDE II | 0.855 | 0.250 |
| 41.55 | 228 | HUMULENE MONO-EPOXIDE III | 0.112 | 0.090 |
| 41.88 | 231 | MW 222 ME 43,79,80 | 0.755 | 0.295 |
| 43.88 | 242 | MW 220 ME 43,79,91 | 0.210 | 0.169 |
| 44.73 | 246 | T-CADINOL | 0.113 | 0.119 |
| 46.08 | 255 | T-MUUROLOL ME 95,121,204 | 0.045 | 0.057 |
| 47.50 | 262 | MW 220 ME 41,67,109 DIEPOXIDE? | 0.000 | 0.000 |
| 48.69 | 268 | FARNESOL | 0.187 | 0.230 |

| GC/ FID RT. | CMPD. # | TENTATIVE IDENTIFICATION BY GC/ MASS SPECTROSCOPY | 21044 NORTHDOWN | 21197 NUGGET |
|---|---|---|---|---|
| 6.42 | 9 | A-PINENE | 0.066 | 0.095 |
| 7.46 | 14 | ISOBUTYL ISOBUTYRATE | 0.000 | 0.244 |
| 8.10 | 16 | 8-PINENE | 0.639 | 0.671 |
| 9.11 | 18 | MYRCENE | 42.280 | 60.676 |
| 9.77 | 22 | 2-METHYL-BUTYL PROPANOATE | 0.106 | 0.559 |
| 9.90 | 23 | ISOAMYL ISOBUTYRATE | 0.000 | 0.550 |
| 9.96 | 24 | 2-METHYL-BUTYL ISOBUTARATE | 0.173 | 1.307 |
| 10.28 | 26 | L-LIMONENE | 0.173 | 0.203 |
| 10.62 | 27 | B-PHELLANDRENE? C10H15 | 0.199 | 0.244 |
| 11.59 | 32 | trans-OCIMENE | 0.104 | 0.571 |
| 12.45 | 35 | 2-METHYL-BUTYL 2-METHYL-BUTYRATE | 0.000 | 0.063 |
| 12.68 | 36 | METHYL HEPTANOATE | 0.337 | 0.615 |
| 12.91 | 40 | ISOAMYL ISOVALERATE | 0.000 | 0.124 |
| 14.31 | 43 | METHYL 4-METHYL-HEXA-2-ENOATE | 0.127 | 0.201 |
| 14.39 | 45 | METHYL 6-METHYL-HEPTANOATE | 0.098 | 0.257 |
| 15.98 | 51 | METHYL OCTANOATE | 0.165 | 0.470 |
| 16.26 | 55 | NONANAL | 0.000 | 0.052 |
| 19.41 | 73 | METHYL NONANOATE | 0.122 | 0.326 |
| 19.56 | 75 | 2-DECANONE, A-YLANGENE | 0.000 | 0.052 |
| 19.93 | 77 | A-COPAENE | 0.321 | 0.167 |
| 21.00 | 83 | LINALOOL | 0.559 | 0.904 |
| 21.31 | 88 | A-GURJUNENE | 0.000 | 0.113 |
| 21.42 | 89 | 7-METHYL-2-DECANONE | 0.000 | 0.000 |
| 22.56 | 93 | C15H24 CALARENE? | 0.228 | 0.069 |
| 22.72 | 95 | A-BERGAMOTENE, METHYL DECANOATE | 0.000 | 0.298 |
| 23.01 | 96 | 2-UNDECANONE | 0.181 | 0.363 |
| 23.10 | 97 | 2-DECANOL | 0.474 | 0.230 |
| 23.44 | 99 | 8-CARYOPHYLLENE | 12.260 | 6.289 |
| 23.84 | 102 | METHYL DEC-4-ENOATE | 0.798 | 1.366 |
| 24.03 | 103 | MW168 2-OL? ME 43,81,110,108 | 0.000 | 0.054 |
| 25.18 | 114 | B-FARNESENE | 0.746 | 0.000 |
| 26.10 | 122 | HUMULENE | 31.313 | 15.386 |
| 26.16 | 123 | METHYL DEC-4,8-DIENOATE | 0.000 | 0.128 |
| 26.46 | 129 | WILEY# 123998 MW 204 C15H24 | 0.198 | 0.359 |
| 26.59 | 131 | 2-DODECANONE | 0.800 | 0.077 |
| 27.32 | 138 | A-FARNESENE OR ZINGIBERENE | 0.210 | 0.321 |
| 27.53 | 139 | CAS# 030021-74-0 | 0.153 | 0.086 |
| 27.75 | 143 | A-MUUROLENE | 0.300 | 0.237 |
| 27.90 | 144 | B-SELINENE | 0.291 | 0.560 |
| 28.04 | 145 | A-SELINENE | 0.324 | 0.647 |
| 28.34 | 147 | METHYL ?-UNDECENOATE | 0.000 | 0.164 |
| 29.16 | 154 | D-CADINENE | 1.517 | 0.760 |
| 29.39 | 155 | G-CADINENE | 0.815 | 0.399 |
| 30.34 | 164 | CAS# 016728-99-7 OR G-SELINENE | 0.146 | 0.102 |
| 30.73 | 166 | A-MUUROLINE | 0.163 | 0.075 |
| 31.15 | 170 | 2-TRIDECANONE | 0.149 | 0.500 |
| 31.36 | 171 | GERANYL PROPANOATE | 0.000 | 0.000 |
| 31.46 | 172 | MW 212 METHYL ?-DODECENOATE | 0.000 | 0.077 |
| 32.28 | 177 | trans-GERANIOL | 0.000 | 0.000 |
| 32.54 | 179 | CAS# 000483-77-2 (CALAMENENE ?) | 0.199 | 0.000 |
| 34.38 | 187 | METHYL 3,6-DODECDIENOATE ME 79 | 0.000 | 0.119 |
| 36.42 | 196 | MW 210 ME 43,54,82 | 0.000 | 0.112 |
| 39.11 | 211 | CARYOPHYLLENE OXIDE | 0.410 | 0.051 |
| 40.23 | 221 | HUMULENE MONO-EPOXIDE I | 0.089 | 0.000 |
| 40.28 | 223 | MW222 ME 43,82 | 0.067 | 0.328 |
| 41.07 | 225 | HUMULENE MONO-EPOXIDE II | 0.801 | 0.113 |
| 41.55 | 228 | HUMULENE MONO-EPOXIDE III | 0.153 | 0.000 |
| 41.88 | 231 | MW 222 ME 43,79,80 | 0.168 | 0.643 |
| 43.88 | 242 | MW 220 ME 43,79,91 | 0.101 | 0.206 |
| 44.73 | 246 | T-CADINOL | 0.138 | 0.062 |
| 46.08 | 255 | T-MUUROLOL ME 95,121,204 | 0.086 | 0.000 |
| 47.50 | 262 | MW 220 ME 41,67,109 DIEPOXIDE? | 0.000 | 0.000 |
| 48.69 | 268 | FARNESOL | 0.154 | 0.071 |

| GC/ FID RT. | CMPD. # | TENTATIVE IDENTIFICATION BY GC/ MASS SPECTROSCOPY | 21223 OLYMPIC | 21227 PERLE |
|---|---|---|---|---|
| 6.42 | 9 | A-PINENE | 0.127 | 0.077 |
| 7.46 | 14 | ISOBUTYL ISOBUTYRATE | 0.116 | 0.193 |
| 8.10 | 16 | 8-PINENE | 1.037 | 0.618 |
| 9.11 | 18 | MYRCENE | 61.466 | 41.489 |
| 9.77 | 22 | 2-METHYL-BUTYL PROPANOATE | 0.470 | 0.120 |
| 9.90 | 23 | ISOAMYL ISOBUTYRATE | 0.121 | 0.000 |
| 9.96 | 24 | 2-METHYL-BUTYL ISOBUTARATE | 1.424 | 0.308 |
| 10.28 | 26 | L-LIMONENE | 0.247 | 0.177 |
| 10.62 | 27 | B-PHELLANDRENE? C10H15 | 0.269 | 0.199 |
| 11.59 | 32 | trans-OCIMENE | 0.040 | 0.591 |
| 12.45 | 35 | 2-METHYL-BUTYL 2-METHYL-BUTYRATE | 0.549 | 0.000 |
| 12.68 | 36 | METHYL HEPTANOATE | 0.136 | 0.425 |
| 12.91 | 40 | ISOAMYL ISOVALERATE | 0.476 | 0.000 |
| 14.31 | 43 | METHYL 4-METHYL-HEXA-2-ENOATE | 0.051 | 0.111 |
| 14.39 | 45 | METHYL 6-METHYL-HEPTANOATE | 0.216 | 0.061 |
| 15.98 | 51 | METHYL OCTANOATE | 0.066 | 0.053 |
| 16.26 | 55 | NONANAL | 0.053 | 0.096 |
| 19.41 | 73 | METHYL NONANOATE | 0.040 | 0.047 |
| 19.56 | 75 | 2-DECANONE, A-YLANGENE | 0.056 | 0.256 |
| 19.93 | 77 | A-COPAENE | 0.201 | 0.350 |
| 21.00 | 83 | LINALOOL | 0.316 | 0.242 |
| 21.31 | 88 | A-GURJUNENE | 0.096 | 0.000 |
| 21.42 | 89 | 7-METHYL-2-DECANONE | 0.000 | 0.047 |
| 22.56 | 93 | C15H24 CALARENE? | 0.093 | 0.224 |
| 22.72 | 95 | A-BERGAMOTENE, METHYL DECANOATE | 0.055 | 0.000 |
| 23.01 | 96 | 2-UNDECANONE | 0.000 | 0.319 |
| 23.10 | 97 | 2-DECANOL | 0.238 | 0.487 |
| 23.44 | 99 | 8-CARYOPHYLLENE | 8.722 | 12.480 |
| 23.84 | 102 | METHYL DEC-4-ENOATE | 0.743 | 0.150 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 24.03 | 103 | MW168 2-OL? ME 43,81,110,108 | 0.000 | 0.096 |
| 25.18 | 114 | B-FARNESENE | 0.000 | 0.162 |
| 26.10 | 122 | HUMULENE | 13.614 | 31.397 |
| 26.16 | 123 | METHYL DEC-4,8-DIENOATE | 0.408 | 0.175 |
| 26.46 | 129 | WILEY# 123998 MW 204 C15H24 | 0.518 | 0.845 |
| 26.59 | 131 | 2-DODECANONE | 0.000 | 0.110 |
| 27.32 | 138 | A-FARNESENE OR ZINGIBERENE | 0.177 | 0.296 |
| 27.53 | 139 | CAS# 030021-74-0 | 0.116 | 0.183 |
| 27.75 | 143 | A-MUUROLENE | 0.248 | 0.315 |
| 27.90 | 144 | B-SELINENE | 0.738 | 0.276 |
| 28.04 | 145 | A-SELINENE | 0.764 | 0.320 |
| 28.34 | 147 | METHYL ?-UNDECENOATE | 0.000 | 0.000 |
| 29.16 | 154 | D-CADINENE | 0.979 | 1.770 |
| 29.39 | 155 | G-CADINENE | 0.547 | 0.862 |
| 30.34 | 164 | CAS# 016728-99-7 OR G-SELINENE | 0.116 | 0.190 |
| 30.73 | 166 | A-MUUROLINE | 0.107 | 0.177 |
| 31.15 | 170 | 2-TRIDECANONE | 0.300 | 0.273 |
| 31.36 | 171 | GERANYL PROPANOATE | 0.105 | 0.000 |
| 31.46 | 172 | MW 212 METHYL ?-DODECENOATE | 0.065 | 0.000 |
| 32.28 | 177 | trans-GERANIOL | 1.055 | 0.000 |
| 32.54 | 179 | CAS# 000483-77-2 (CALAMENENE ?) | 0.084 | 0.123 |
| 34.38 | 187 | METHYL 3,6-DODECDIENOATE ME 79 | 0.063 | 0.000 |
| 36.42 | 196 | MW 210 ME 43,54,82 | 0.000 | 0.077 |
| 39.11 | 211 | CARYOPHYLLENE OXIDE | 0.166 | 0.152 |
| 40.23 | 221 | HUMULENE MONO-EPOXIDE I | 0.059 | 0.072 |
| 40.28 | 223 | MW222 ME 43,82 | 0.113 | 0.100 |
| 41.07 | 225 | HUMULENE MONO-EPOXIDE II | 0.224 | 0.366 |
| 41.55 | 228 | HUMULENE MONO-EPOXIDE III | 0.076 | 0.136 |
| 41.88 | 231 | MW 222 ME 43,79,80 | 0.253 | 0.389 |
| 43.88 | 242 | MW 220 ME 43,79,91 | 0.139 | 0.276 |
| 44.73 | 246 | T-CADINOL | 0.097 | 0.186 |
| 46.08 | 255 | T-MUUROLOL ME 95,121,204 | 0.057 | 0.115 |
| 47.50 | 262 | MW 220 ME 41,67,109 DIEPOXIDE? | 0.000 | 0.000 |
| 48.69 | 268 | FARNESOL | 0.127 | 0.192 |

| GC/ FID RT. | CMPD. # | TENTATIVE IDENTIFICATION BY GC/ MASS SPECTROSCOPY | 60052 PRIDE OF RINGWOOD | 21077 SAAZ |
|---|---|---|---|---|
| 6.42 | 9 | A-PINENE | 0.089 | 0.049 |
| 7.46 | 14 | ISOBUTYL ISOBUTYRATE | 0.043 | 0.000 |
| 8.10 | 16 | 8-PINENE | 0.690 | 0.486 |
| 9.11 | 18 | MYRCENE | 46.727 | 34.050 |
| 9.77 | 22 | 2-METHYL-BUTYL PROPANOATE | 0.121 | 0.000 |
| 9.90 | 23 | ISOAMYL ISOBUTYRATE | 0.000 | 0.000 |
| 9.96 | 24 | 2-METHYL-BUTYL ISOBUTARATE | 0.220 | 0.000 |
| 10.28 | 26 | L-LIMONENE | 0.197 | 0.166 |
| 10.62 | 27 | B-PHELLANDRENE? C10H15 | 0.156 | 0.081 |
| 11.59 | 32 | trans-OCIMENE | 0.000 | 0.000 |
| 12.45 | 35 | 2-METHYL-BUTYL 2-METHYL-BUTYRATE | 0.000 | 0.000 |
| 12.68 | 36 | METHYL HEPTANOATE | 0.334 | 0.626 |
| 12.91 | 40 | ISOAMYL ISOVALERATE | 0.000 | 0.000 |
| 14.31 | 43 | METHYL 4-METHYL-HEXA-2-ENOATE | 0.180 | 0.258 |
| 14.39 | 45 | METHYL 6-METHYL-HEPTANOATE | 0.319 | 0.340 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 15.98 | 51 | METHYL OCTANOATE | 0.473 | 0.225 |
| 16.26 | 55 | NONANAL | 0.116 | 0.308 |
| 19.41 | 73 | METHYL NONANOATE | 0.250 | 0.380 |
| 19.56 | 75 | 2-DECANONE, A-YLANGENE | 0.147 | 0.501 |
| 19.93 | 77 | A-COPAENE | 0.241 | 0.191 |
| 21.00 | 83 | LINALOOL | 0.317 | 0.337 |
| 21.31 | 88 | A-GURJUNENE | 0.230 | 0.173 |
| 21.42 | 89 | 7-METHYL-2-DECANONE | 0.125 | 0.222 |
| 22.56 | 93 | C15H24 CALARENE? | 0.133 | 0.113 |
| 22.72 | 95 | A-BERGAMOTENE, METHYL DECANOATE | 0.326 | 1.043 |
| 23.01 | 96 | 2-UNDECANONE | 0.690 | 1.394 |
| 23.10 | 97 | 2-DECANOL | 0.226 | 0.299 |
| 23.44 | 99 | 8-CARYOPHYLLENE | 8.708 | 5.010 |
| 23.84 | 102 | METHYL DEC-4-ENOATE | 1.808 | 1.769 |
| 24.03 | 103 | MW168 2-OL? ME 43,81,110,108 | 0.230 | 0.417 |
| 25.18 | 114 | B-FARNESENE | 0.000 | 18.900 |
| 26.10 | 122 | HUMULENE | 1.946 | 18.111 |
| 26.16 | 123 | METHYL DEC-4,8-DIENOATE | 0.571 | 0.259 |
| 26.46 | 129 | WILEY# 123998 MW 204 C15H24 | 0.680 | 0.531 |
| 26.59 | 131 | 2-DODECANONE | 0.053 | 0.264 |
| 27.32 | 138 | A-FARNESENE OR ZINGIBERENE | 1.932 | 0.255 |
| 27.53 | 139 | CAS# 030021-74-0 | 0.000 | 0.134 |
| 27.75 | 143 | A-MUUROLENE | 0.000 | 0.189 |
| 27.90 | 144 | B-SELINENE | 9.372 | 0.255 |
| 28.04 | 145 | A-SELINENE | 10.128 | 0.178 |
| 28.34 | 147 | METHYL ?-UNDECENOATE | 1.329 | 0.104 |
| 29.16 | 154 | D-CADINENE | 1.124 | 0.829 |
| 29.39 | 155 | G-CADINENE | 0.650 | 0.519 |
| 30.34 | 164 | CAS# 016728-99-7 OR G-SELINENE | 0.137 | 0.181 |
| 30.73 | 166 | A-MUUROLINE | 0.133 | 0.099 |
| 31.15 | 170 | 2-TRIDECANONE | 0.551 | 0.957 |
| 31.36 | 171 | GERANYL PROPANOATE | 0.000 | 0.000 |
| 31.46 | 172 | MW 212 METHYL ?-DODECENOATE | 0.104 | 0.081 |
| 32.28 | 177 | trans-GERANIOL | 0.217 | 0.080 |
| 32.54 | 179 | CAS# 000483-77-2 (CALAMENENE ?) | 0.146 | 0.167 |
| 34.38 | 187 | METHYL 3,6-DODECDIENOATE ME 79 | 0.182 | 0.424 |
| 36.42 | 196 | MW 210 ME 43,54,82 | 0.079 | 0.272 |
| 39.11 | 211 | CARYOPHYLLENE OXIDE | 0.337 | 0.476 |
| 40.23 | 221 | HUMULENE MONO-EPOXIDE I | 0.076 | 0.329 |
| 40.28 | 223 | MW222 ME 43,82 | 0.175 | 0.294 |
| 41.07 | 225 | HUMULENE MONO-EPOXIDE II | 0.106 | 1.530 |
| 41.55 | 228 | HUMULENE MONO-EPOXIDE III | 0.082 | 0.155 |
| 41.88 | 231 | MW 222 ME 43,79,80 | 0.852 | 1.789 |
| 43.88 | 242 | MW 220 ME 43,79,91 | 0.231 | 0.487 |
| 44.73 | 246 | T-CADINOL | 0.140 | 0.174 |
| 46.08 | 255 | T-MUUROLOL ME 95,121,204 | 0.067 | 0.099 |
| 47.50 | 262 | MW 220 ME 41,67,109 DIEPOXIDE? | 0.000 | 0.083 |
| 48.69 | 268 | FARNESOL | 0.169 | 0.160 |

| GC/ FID RT. | CMPD. # | TENTATIVE IDENTIFICATION BY GC/ MASS SPECTROSCOPY | 21186 SPALTER | 21173 STRISS-LESPALT |
|---|---|---|---|---|
| 6.42 | 9 | A-PINENE | 0.091 | 0.062 |
| 7.46 | 14 | ISOBUTYL ISOBUTYRATE | 0.000 | 0.202 |
| 8.10 | 16 | 8-PINENE | 0.861 | 0.634 |
| 9.11 | 18 | MYRCENE | 60.356 | 43.977 |
| 9.77 | 22 | 2-METHYL-BUTYL | 0.000 | 0.257 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| | | PROPANOATE | | |
| 9.90 | 23 | ISOAMYL ISOBUTYRATE | 0.000 | 0.112 |
| 9.96 | 24 | 2-METHYL-BUTYL ISOBUTARATE | 0.000 | 0.736 |
| 10.28 | 26 | L-LIMONENE | 0.225 | 0.175 |
| 10.62 | 27 | B-PHELLANDRENE? C10H15 | 0.234 | 0.139 |
| 11.59 | 32 | trans-OCIMENE | 0.055 | 0.082 |
| 12.45 | 35 | 2-METHYL-BUTYL 2-METHYL-BUTYRATE | 0.000 | 0.000 |
| 12.68 | 36 | METHYL HEPTANOATE | 0.658 | 0.326 |
| 12.91 | 40 | ISOAMYL ISOVALERATE | 0.000 | 0.000 |
| 14.31 | 43 | METHYL 4-METHYL-HEXA-2-ENOATE | 0.238 | 0.323 |
| 14.39 | 45 | METHYL 6-METHYL-HEPTANOATE | 0.230 | 0.000 |
| 15.98 | 51 | METHYL OCTANOATE | 0.168 | 0.103 |
| 16.26 | 55 | NONANAL | 0.166 | 0.255 |
| 19.41 | 73 | METHYL NONANOATE | 0.341 | 0.119 |
| 19.56 | 75 | 2-DECANONE, A-YLANGENE | 0.313 | 0.216 |
| 19.93 | 77 | A-COPAENE | 0.090 | 0.293 |
| 21.00 | 83 | LINALOOL | 0.557 | 0.649 |
| 21.31 | 88 | A-GURJUNENE | 0.127 | 0.000 |
| 21.42 | 89 | 7-METHYL-2-DECANONE | 0.144 | 0.133 |
| 22.56 | 93 | C15H24 CALARENE? | 0.055 | 0.243 |
| 22.72 | 95 | A-BERGAMOTENE, METHYL DECANOATE | 0.691 | 0.000 |
| 23.01 | 96 | 2-UNDECANONE | 0.612 | 0.385 |
| 23.10 | 97 | 2-DECANOL | 0.179 | 0.509 |
| 23.44 | 99 | 8-CARYOPHYLLENE | 2.481 | 10.500 |
| 23.84 | 102 | METHYL DEC-4-ENOATE | 1.180 | 0.570 |
| 24.03 | 103 | MW168 2-OL? ME 43,81,110,108 | 0.211 | 0.091 |
| 25.18 | 114 | B-FARNESENE | 14.019 | 0.000 |
| 26.10 | 122 | HUMULENE | 9.083 | 29.252 |
| 26.16 | 123 | METHYL DEC-4,8-DIENOATE | 0.313 | 0.147 |
| 26.46 | 129 | WILEY# 123998 MW 204 C15H24 | 0.243 | 0.872 |
| 26.59 | 131 | 2-DODECANONE | 0.174 | 0.000 |
| 27.32 | 138 | A-FARNESENE OR ZINGIBERENE | 0.179 | 0.131 |
| 27.53 | 139 | CAS# 030021-74-0 | 0.000 | 0.088 |
| 27.75 | 143 | A-MUUROLENE | 0.137 | 0.233 |
| 27.90 | 144 | B-SELINENE | 0.130 | 0.237 |
| 28.04 | 145 | A-SELINENE | 0.069 | 0.281 |
| 28.34 | 147 | METHYL ?-UNDECENOATE | 0.118 | 0.082 |
| 29.16 | 154 | D-CADINENE | 0.398 | 1.364 |
| 29.39 | 155 | G-CADINENE | 0.226 | 0.824 |
| 30.34 | 164 | CAS# 016728-99-7 OR G-SELINENE | 0.119 | 0.210 |
| 30.73 | 166 | A-MUUROLINE | 0.000 | 0.196 |
| 31.15 | 170 | 2-TRIDECANONE | 0.479 | 0.255 |
| 31.36 | 171 | GERANYL PROPANOATE | 0.000 | 0.000 |
| 31.46 | 172 | MW 212 METHYL ?-DODECENOATE | 0.063 | 0.000 |
| 32.28 | 177 | trans-GERANIOL | 0.193 | 0.000 |
| 32.54 | 179 | CAS# 000483-77-2 (CALAMENENE ?) | 0.073 | 0.205 |
| 34.38 | 187 | METHYL 3,6-DODECDIENOATE ME 79 | 0.233 | 0.000 |
| 36.42 | 196 | MW 210 ME 43,54,82 | 0.155 | 0.172 |
| 39.11 | 211 | CARYOPHYLLENE OXIDE | 0.139 | 0.540 |
| 40.23 | 221 | HUMULENE MONO-EPOXIDE I | 0.106 | 0.152 |
| 40.28 | 223 | MW222 ME 43,82 | 0.137 | 0.150 |
| 41.07 | 225 | HUMULENE MONO-EPOXIDE II | 0.425 | 1.140 |
| 41.55 | 228 | HUMULENE MONO-EPOXIDE III | 0.000 | 0.000 |
| 41.88 | 231 | MW 222 ME 43,79,80 | 0.854 | 0.609 |
| 43.88 | 242 | MW 220 ME 43,79,91 | 0.186 | 0.141 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 44.73 | 246 | T-CADINOL | 0.064 | 0.144 |
| 46.08 | 255 | T-MUUROLOL ME 95,121,204 | 0.000 | 0.092 |
| 47.50 | 262 | MW 220 ME 41,67,109 DIEPOXIDE? | 0.000 | 0.000 |
| 48.69 | 268 | FARNESOL | 0.093 | 0.191 |

| GC/ FID RT. | CMPD. # | TENTATIVE IDENTIFICATION BY GC/MASS SPECTROSCOPY | 21049 STYRIAN | 21112 TARGET |
|---|---|---|---|---|
| 6.42 | 9 | A-PINENE | 0.089 | 0.119 |
| 7.46 | 14 | ISOBUTYL ISOBUTYRATE | 0.328 | 0.406 |
| 8.10 | 16 | 8-PINENE | 0.795 | 0.865 |
| 9.11 | 18 | MYRCENE | 56.296 | 58.164 |
| 9.77 | 22 | 2-METHYL-BUTYL PROPANOATE | 0.171 | 0.482 |
| 9.90 | 23 | ISOAMYL ISOBUTYRATE | 0.000 | 0.461 |
| 9.96 | 24 | 2-METHYL-BUTYL ISOBUTARATE | 0.753 | 1.408 |
| 10.28 | 26 | L-LIMONENE | 0.207 | 0.228 |
| 10.62 | 27 | B-PHELLANDRENE? C10H15 | 0.229 | 0.226 |
| 11.59 | 32 | trans-OCIMENE | 0.057 | 0.366 |
| 12.45 | 35 | 2-METHYL-BUTYL 2-METHYL-BUTYRATE | 0.000 | 0.054 |
| 12.68 | 36 | METHYL HEPTANOATE | 0.270 | 0.602 |
| 12.91 | 40 | ISOAMYL ISOVALERATE | 0.000 | 0.118 |
| 14.31 | 43 | METHYL 4-METHYL-HEXA-2-ENOATE | 0.305 | 0.427 |
| 14.39 | 45 | METHYL 6-METHYL-HEPTANOATE | 0.000 | 0.589 |
| 15.98 | 51 | METHYL OCTANOATE | 0.000 | 0.446 |
| 16.26 | 55 | NONANAL | 0.141 | 0.107 |
| 19.41 | 73 | METHYL NONANOATE | 0.070 | 0.689 |
| 19.56 | 75 | 2-DECANONE, A-YLANGENE | 0.216 | 0.821 |
| 19.93 | 77 | A-COPAENE | 0.198 | 0.336 |
| 21.00 | 83 | LINALOOL | 0.751 | 0.891 |
| 21.31 | 88 | A-GURJUNENE | 0.000 | 0.000 |
| 21.42 | 89 | 7-METHYL-2-DECANONE | 0.094 | 0.401 |
| 22.56 | 93 | C15H24 CALARENE? | 0.166 | 0.000 |
| 22.72 | 95 | A-BERGAMOTENE, METHYL DECANOATE | 0.266 | 0.519 |
| 23.01 | 96 | 2-UNDECANONE | 0.301 | 1.502 |
| 23.10 | 97 | 2-DECANOL | 0.366 | 0.282 |
| 23.44 | 99 | 8-CARYOPHYLLENE | 7.269 | 4.952 |
| 23.84 | 102 | METHYL DEC-4-ENOATE | 0.196 | 1.912 |
| 24.03 | 103 | MW168 2-OL? ME 43,81,110,108 | 0.096 | 0.214 |
| 25.18 | 114 | B-FARNESENE | 4.187 | 0.000 |
| 26.10 | 122 | HUMULENE | 20.607 | 10.291 |
| 26.16 | 123 | METHYL DEC-4,8-DIENOATE | 0.106 | 0.221 |
| 26.46 | 129 | WILEY# 123998 MW 204 C15H24 | 0.527 | 1.123 |
| 26.59 | 131 | 2-DODECANONE | 0.000 | 0.000 |
| 27.32 | 138 | A-FARNESENE OR ZINGIBERENE | 0.000 | 0.233 |
| 27.53 | 139 | CAS# 030021-74-0 | 0.000 | 0.165 |
| 27.75 | 143 | A-MUUROLENE | 0.211 | 0.215 |
| 27.90 | 144 | B-SELINENE | 0.152 | 0.329 |
| 28.04 | 145 | A-SELINENE | 0.184 | 0.404 |
| 28.34 | 147 | METHYL ?-UNDECENOATE | 0.269 | 0.000 |
| 29.16 | 154 | D-CADINENE | 0.013 | 1.215 |
| 29.39 | 155 | G-CADINENE | 0.536 | 0.653 |
| 30.34 | 164 | CAS# 016728-99-7 OR G-SELINENE | 0.000 | 0.798 |
| 30.73 | 166 | A-MUUROLINE | 0.167 | 0.198 |
| 31.15 | 170 | 2-TRIDECANONE | 0.228 | 0.974 |
| 31.36 | 171 | GERANYL PROPANOATE | 0.000 | 0.000 |
| 31.46 | 172 | MW 212 METHYL ?-DODECENOATE | 0.000 | 0.114 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 32.28 | 177 | trans-GERANIOL | 0.000 | 0.000 |
| 32.54 | 179 | CAS# 000483-77-2 (CALAMENENE ?) | 0.112 | 0.118 |
| 34.38 | 187 | METHYL 3,6-DODECDIENOATE ME 79 | 0.000 | 0.388 |
| 36.42 | 196 | MW 210 ME 43,54,82 | 0.000 | 0.460 |
| 39.11 | 211 | CARYOPHYLLENE OXIDE | 0.265 | 0.095 |
| 40.23 | 221 | HUMULENE MONO-EPOXIDE I | 0.000 | 0.536 |
| 40.28 | 223 | MW222 ME 43,82 | 0.000 | 0.000 |
| 41.07 | 225 | HUMULENE MONO-EPOXIDE II | 0.569 | 0.210 |
| 41.55 | 228 | HUMULENE MONO-EPOXIDE III | 0.000 | 0.000 |
| 41.88 | 231 | MW 222 ME 43,79,80 | 0.394 | 1.253 |
| 43.88 | 242 | MW 220 ME 43,79,91 | 0.119 | 0.266 |
| 44.73 | 246 | T-CADINOL | 0.119 | 0.114 |
| 46.08 | 255 | T-MUUROLOL ME 95,121,204 | 0.000 | 0.000 |
| 47.50 | 262 | MW 220 ME 41,67,109 DIEPOXIDE? | 0.000 | 0.000 |
| 48.69 | 268 | FARNESOL | 0.000 | 0.000 |

| GC/ FID RT. | CMPD. # | TENTATIVE IDENTIFICATION BY GC/ MASS SPECTROSCOPY | 21015 TETT-NANG | 21041 WTILAM-EITF |
|---|---|---|---|---|
| 6.42 | 9 | A-PINENE | 0.080 | 0.078 |
| 7.46 | 14 | ISOBUTYL ISOBUTYRATE | 0.000 | 0.217 |
| 8.10 | 16 | 8-PINENE | 0.753 | 0.741 |
| 9.11 | 18 | MYRCENE | 50.137 | 55.492 |
| 9.77 | 22 | 2-METHYL-BUTYL PROPANOATE | 0.000 | 0.234 |
| 9.90 | 23 | ISOAMYL ISOBUTYRATE | 0.000 | 0.000 |
| 9.96 | 24 | 2-METHYL-BUTYL ISOBUTARATE | 0.000 | 0.507 |
| 10.28 | 26 | L-LIMONENE | 0.205 | 0.191 |
| 10.62 | 27 | B-PHELLANDRENE? C10H15 | 0.147 | 0.251 |
| 11.59 | 32 | trans-OCIMENE | 0.000 | 0.114 |
| 12.45 | 35 | 2-METHYL-BUTYL 2-METHYL-BUTYRATE | 0.000 | 0.000 |
| 12.68 | 36 | METHYL HEPTANOATE | 0.509 | 0.532 |
| 12.91 | 40 | ISOAMYL ISOVALERATE | 0.000 | 0.000 |
| 14.31 | 43 | METHYL 4-METHYL-HEXA-2-ENOATE | 0.230 | 0.224 |
| 14.39 | 45 | METHYL 6-METHYL-HEPTANOATE | 0.260 | 0.120 |
| 15.98 | 51 | METHYL OCTANOATE | 0.172 | 0.087 |
| 16.26 | 55 | NONANAL | 0.233 | 0.073 |
| 19.41 | 73 | METHYL NONANOATE | 0.228 | 0.078 |
| 19.56 | 75 | 2-DECANONE, A-YLANGENE | 0.290 | 0.097 |
| 19.93 | 77 | A-COPAENE | 0.129 | 0.190 |
| 21.00 | 83 | LINALOOL | 0.441 | 0.661 |
| 21.31 | 88 | A-GURJUNENE | 0.125 | 0.000 |
| 21.42 | 89 | 7-METHYL-2-DECANONE | 0.199 | 0.000 |
| 22.56 | 93 | C15H24 CALARENE? | 0.085 | 0.141 |
| 22.72 | 95 | A-BERGAMOTENE, METHYL DECANOATE | 0.873 | 0.380 |
| 23.01 | 96 | 2-UNDECANONE | 0.759 | 0.131 |
| 23.10 | 97 | 2-DECANOL | 0.257 | 0.313 |
| 23.44 | 99 | 8-CARYOPHYLLENE | 3.697 | 6.934 |
| 23.84 | 102 | METHYL DEC-4-ENOATE | 1.220 | 0.288 |
| 24.03 | 103 | MW168 2-OL? ME 43,81,110,108 | 0.255 | 0.041 |
| 25.18 | 114 | B-FARNESENE | 16.938 | 7.097 |
| 26.10 | 122 | HUMULENE | 13.277 | 18.815 |
| 26.16 | 123 | METHYL DEC-4,8-DIENOATE | 0.338 | 0.196 |
| 26.46 | 129 | WILEY# 123998 MW 204 C15H24 | 0.321 | 0.472 |
| 26.59 | 131 | 2-DODECANONE | 0.169 | 0.000 |
| 27.32 | 138 | A-FARNESENE OR ZINGIBERENE | 0.194 | 0.599 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 27.53 | 139 | CAS# 030021-74-0 | 0.000 | 0.106 |
| 27.75 | 143 | A-MUUROLENE | 0.121 | 0.170 |
| 27.90 | 144 | B-SELINENE | 0.166 | 0.245 |
| 28.04 | 145 | A-SELINENE | 0.099 | 0.238 |
| 28.34 | 147 | METHYL ?-UNDECENOATE | 0.177 | 0.407 |
| 29.16 | 154 | D-CADINENE | 0.532 | 0.970 |
| 29.39 | 155 | G-CADINENE | 0.317 | 0.493 |
| 30.34 | 164 | CAS# 016728-99-7 OR G-SELINENE | 0.114 | 0.107 |
| 30.73 | 166 | A-MUUROLINE | 0.059 | 0.099 |
| 31.15 | 170 | 2-TRIDECANONE | 0.574 | 0.142 |
| 31.36 | 171 | GERANYL PROPANOATE | 0.000 | 0.000 |
| 31.46 | 172 | MW 212 METHYL ?-DODECENOATE | 0.000 | 0.000 |
| 32.28 | 177 | trans-GERANIOL | 0.157 | 0.050 |
| 32.54 | 179 | CAS# 000483-77-2 (CALAMENENE ?) | 0.131 | 0.071 |
| 34.38 | 187 | METHYL 3,6-DODECDIENOATE ME 79 | 0.192 | 0.000 |
| 36.42 | 196 | MW 210 ME 43,54,82 | 0.163 | 0.000 |
| 39.11 | 211 | CARYOPHYLLENE OXIDE | 0.282 | 0.097 |
| 40.23 | 221 | HUMULENE MONO-EPOXIDE I | 0.180 | 0.000 |
| 40.28 | 223 | MW222 ME 43,82 | 0.161 | 0.000 |
| 41.07 | 225 | HUMULENE MONO-EPOXIDE II | 0.901 | 0.200 |
| 41.55 | 228 | HUMULENE MONO-EPOXIDE III | 0.089 | 0.071 |
| 41.88 | 231 | MW 222 ME 43,79,80 | 1.033 | 0.118 |
| 43.88 | 242 | MW 220 ME 43,79,91 | 0.235 | 0.000 |
| 44.73 | 246 | T-CADINOL | 0.098 | 0.104 |
| 46.08 | 255 | T-MUUROLOL ME 95,121,204 | 0.000 | 0.061 |
| 47.50 | 262 | MW 220 ME 41,67,109 DIEPOXIDE? | 0.000 | 0.000 |
| 48.69 | 268 | FARNESOL | 0.131 | 0.457 |

| GC/ FID RT. | CMPD. # | TENTATIVE IDENTIFICATION BY GC/ MASS SPECTROSCOPY | 21498 YEOMAN | 9/17 COLUMBUS |
|---|---|---|---|---|
| 6.42 | 9 | A-PINENE | 0.121 | 0.125 |
| 7.46 | 14 | ISOBUTYL ISOBUTYRATE | 0.455 | 0.066 |
| 8.10 | 16 | 8-PINENE | 0.829 | 0.745 |
| 9.11 | 18 | MYRCENE | 51.427 | 42.267 |
| 9.77 | 22 | 2-METHYL-BUTYL PROPANOATE | 0.659 | 0.370 |
| 9.90 | 23 | ISOAMYL ISOBUTYRATE | 0.522 | 0.184 |
| 9.96 | 24 | 2-METHYL-BUTYL ISOBUTARATE | 1.946 | 0.800 |
| 10.28 | 26 | L-LIMONENE | 0.237 | 0.236 |
| 10.62 | 27 | B-PHELLANDRENE? C10H15 | 0.260 | 0.177 |
| 11.59 | 32 | trans-OCIMENE | 0.159 | 0.168 |
| 12.45 | 35 | 2-METHYL-BUTYL 2-METHYL-BUTYRATE | 0.180 | 0.090 |
| 12.68 | 36 | METHYL HEPTANOATE | 0.349 | 0.000 |
| 12.91 | 40 | ISOAMYL ISOVALERATE | 0.274 | 0.106 |
| 14.31 | 43 | METHYL 4-METHYL-HEXA-2-ENOATE | 0.139 | 0.000 |
| 14.39 | 45 | METHYL 6-METHYL-HEPTANOATE | 0.119 | 0.153 |
| 15.98 | 51 | METHYL OCTANOATE | 0.209 | 0.000 |
| 16.26 | 55 | NONANAL | 0.059 | 0.000 |
| 19.41 | 73 | METHYL NONANOATE | 0.070 | 0.000 |
| 19.56 | 75 | 2-DECANONE, A-YLANGENE | 0.133 | |
| 19.93 | 77 | A-COPAENE | 0.252 | 0.764 |
| 21.00 | 83 | LINALOOL | 0.379 | 0.417 |
| 21.31 | 88 | A-GURJUNENE | 0.000 | |
| 21.42 | 89 | 7-METHYL-2-DECANONE | 0.000 | 0.000 |
| 22.56 | 93 | C15H24 CALARENE? | 0.123 | 0.252 |

APPENDIX 1-continued

Detailed GLC analysis of assorted hop varieties.
Analytical Conditions: see Kenny (1990), supra.
OIL AREA PERCENTS OF COMMERCIAL HOPS

| | | | | |
|---|---|---|---|---|
| 22.72 | 95 | A-BERGAMOTENE, METHYL DECANOATE | 0.000 | 0.000 |
| 23.01 | 96 | 2-UNDECANONE | 0.361 | 0.068 |
| 23.10 | 97 | 2-DECANOL | 0.268 | |
| 23.44 | 99 | 8-CARYOPHYLLENE | 6.954 | 10.236 |
| 23.84 | 102 | METHYL DEC-4-ENOATE | 0.692 | 0.457 |
| 24.03 | 103 | MW168 2-OL? ME 43,81,110,108 | 0.115 | 0.000 |
| 25.18 | 114 | B-FARNESENE | 0.000 | 0.000 |
| 26.10 | 122 | HUMULENE | 10.146 | 17.370 |
| 26.16 | 123 | METHYL DEC-4,8-DIENOATE | 0.553 | |
| 26.46 | 129 | WILEY# 123998 MW 204 C15H24 | 0.439 | 1.992 |
| 26.59 | 131 | 2-DODECANONE | 0.045 | 0.000 |
| 27.32 | 138 | A-FARNESENE OR ZINGIBERENE | 0.223 | 0.508 |
| 27.53 | 139 | CAS# 030021-74-0 | 0.117 | 0.464 |
| 27.75 | 143 | A-MUUROLENE | 0.209 | 0.733 |
| 27.90 | 144 | B-SELINENE | 2.829 | 1.230 |
| 28.04 | 145 | A-SELINENE | 3.352 | 1.291 |
| 28.34 | 147 | METHYL ?-UNDECENOATE | 0.075 | 0.000 |
| 29.16 | 154 | D-CADINENE | 1.028 | 3.412 |
| 29.39 | 155 | G-CADINENE | 0.484 | 2.048 |
| 30.34 | 164 | CAS# 016728-99-7 OR G-SELINENE | 0.134 | 2.809 |
| 30.73 | 166 | A-MUUROLINE | 0.095 | 0.366 |
| 31.15 | 170 | 2-TRIDECANONE | 0.313 | 0.000 |
| 31.36 | 171 | GERANYL PROPANOATE | 0.000 | 0.753 |
| 31.46 | 172 | MW 212 METHYL ?-DODECENOATE | 0.000 | 0.000 |
| 32.28 | 177 | trans-GERANIOL | 0.363 | 0.180 |
| 32.54 | 179 | CAS# 000483-77-2 (CALAMENENE ?) | 0.069 | 0.381 |
| 34.38 | 187 | METHYL 3,6-DODECDIENOATE ME 79 | 0.061 | 0.000 |
| 36.42 | 196 | MW 210 ME 43,54,82 | 0.048 | 0.135 |
| 39.11 | 211 | CARYOPHYLLENE OXIDE | 0.061 | 0.235 |
| 40.23 | 221 | HUMULENE MONO-EPOXIDE I | 0.059 | 0.109 |
| 40.28 | 223 | MW222 ME 43,82 | 0.078 | |
| 41.07 | 225 | HUMULENE MONO-EPOXIDE II | 0.161 | 0.358 |
| 41.55 | 228 | HUMULENE MONO-EPOXIDE III | 0.073 | 0.167 |
| 41.88 | 231 | MW 222 ME 43,79,80 | 0.365 | 0.847 |
| 43.88 | 242 | MW 220 ME 43,79,91 | 0.000 | 0.455 |
| 44.73 | 246 | T-CADINOL | 0.101 | 0.232 |
| 46.08 | 255 | T-MUUROLOL ME 95,121,204 | 0.062 | 0.111 |
| 47.50 | 262 | MW 220 ME 41,67,109 DIEPOXIDE? | 0.000 | 0.112 |
| 48.69 | 268 | FARNESOL | 0.148 | |

APPENDIX 2

Detailed GLC analyses of Columbus and other U.S. high alpha hops.

| Identification | Group | COLUMBUS 92-12-8-2 | Area % GALENA 92-12-8-3 |
|---|---|---|---|
| Apha-Pinene | | 0.125 | 0.184 |
| Beta-Pinene | 1 | 0.943 | 0.883 |
| Myrcene | 1 | 51.571 | 66.560 |
| Methyl butyl Isobutyrate | | 0.838 | 3.575 |
| Limonene | 4 | 0.288 | 0.350 |
| Linalool | 3 | 0.470 | 0.294 |
| Caryophyllene | 1 | 6.297 | 3.097 |
| Farnesene? | 1 | 0.275 | 0.112 |
| Humulene | 1 | 11.049 | 5.764 |

APPENDIX 2-continued

Detailed GLC analyses of Columbus and other U.S. high alpha hops.

| | | | |
|---|---|---|---|
| Muurolene | 4 | 0.768 | 0.309 |
| Selinene | 4 | 1.472 | 0.341 |
| Geranyl Acetate | 3 | 0.016 | 0.048 |
| delta Cadinene | 4 | 1.834 | 0.292 |
| Gamma Cadinene | 4 | 1.095 | 0.143 |
| Geranyl Isobutyrate | 3 | 1.716 | 0.296 |
| Undecanone-2 | | 1.348 | 0.059 |
| Geraniol | 3 | 0.048 | 0.060 |
| Limonen-10-ol | | 0.155 | 0.021 |
| Caryophyllene oxide | 2 | 0.259 | 0.014 |
| Humulene epoxide I | 2 | 0.430 | 0.033 |
| Humulene epoxide II | 2 | 1.450 | 0.068 |
| Caryolan-i-ol | 2 | 0.120 | 0.006 |
| Humulene epoxide III | 2 | 0.025 | 0.013 |
| Humulol | 2 | 0.185 | 0.011 |
| beta Eudesmol? | | | |
| alpha Eudesmol? | | | |
| Humulenol II | 2 | 0.103 | |
| Humulene diepoxide? | 2 | | |
| Major Hydrocarbons (1) | | 70.135 | 76.216 |
| Oxidation Products (2) | | 2.572 | 0.145 |
| Floral-Estery (3) | | 2.250 | 0.698 |
| Citrus Piney (4) | | 5.457 | 1.435 |
| Total Accounted For | | 80.414 | 78.494 |
| Humulene/Caryophyllene | | 1.753 | 1.861 |

| Identification | Group | CHINOOK 92-12-9-1 | NUGGET 92-12-9-2 |
|---|---|---|---|
| Apha-Pinene | | 0.047 | 0.081 |
| Beta-Pinene | 1 | 0.435 | 0.667 |
| Myrcene | 1 | 28.469 | 51.972 |
| Methyl butyl Isobutyrate | | 1.410 | 1.274 |
| Limonene | 4 | 0.136 | 0.183 |
| Linalool | 3 | 0.369 | 1.022 |
| Caryophyllene | 1 | 9.516 | 8.597 |
| Farnesene? | 1 | 0.353 | 0.162 |
| Humulene | 1 | 21.157 | 19.029 |
| Muurolene | 4 | 1.517 | 0.921 |
| Selinene | 4 | 1.385 | 0.818 |
| Geranyl Acetate | 3 | 0.210 | 0.044 |
| delta Cadinene | 4 | 4.215 | 0.926 |
| Gamma Cadinene | 4 | 2.686 | 0.445 |
| Geranyl Isobutyrate | 3 | 3.323 | 0.076 |
| Undecanone-2 | | 0.675 | 0.453 |
| Geraniol | 3 | 0.155 | 0.079 |
| Limonen-10-ol | | 0.049 | 0.037 |
| Caryophyllene oxide | 2 | 0.076 | 0.032 |
| Humulene epoxide I | 2 | 0.326 | 0.220 |
| Humulene epoxide II | 2 | 0.663 | 0.328 |
| Caryolan-i-ol | 2 | 0.088 | 0.015 |
| Humulene epoxide III | 2 | 0.033 | |
| Humulol | 2 | 0.379 | 0.040 |
| beta Eudesmol? | | 0.248 | |
| alpha Eudesmol? | | 0.205 | |
| Humulenol II | 2 | 0.112 | 0.022 |
| Humulene diepoxide? | 2 | 0.316 | |
| Major Hydrocarbons (1) | | 59.924 | 80.427 |
| Oxidation Products (2) | | 1.993 | 0.657 |
| Floral-Estery (3) | | 4.057 | 1.221 |
| Citrus Piney (4) | | 9.939 | 3.293 |
| Total Accounted For | | 75.913 | 85.598 |
| Humulene/Caryophyllene | | 2.223 | 2.213 |

Area Percent Report
Sample Name: 92-12-8-2

| Pk # | Ret Time | Area | Area % | Identification |
|---|---|---|---|---|
| 1 | 7.030 | 3884 | 0.031 | |
| 2 | 7.854 | 1456 | 0.011 | |
| 3 | 8.010 | 1580 | 0.012 | |
| 4 | 9.053 | 8364 | 0.066 | |
| 5 | 9.260 | 10821 | 0.086 | |
| 6 | 9.358 | 15718 | 0.125 | Alpha-Pinene |
| 7 | 9.800 | 4213 | 0.033 | |

APPENDIX 2-continued

Detailed GLC analyses of Columbus and other U.S. high alpha hops.

| | | | | |
|---|---|---|---|---|
| 8 | 10.297 | 2957 | 0.023 | |
| 9 | 10.543 | 9679 | 0.077 | |
| 10 | 11.097 | 967 | 0.007 | |
| 11 | 11.242 | 118386 | 0.943 | Beta-Pinene |
| 12 | 11.904 | 1183 | 0.009 | |
| 13 | 12.476 | 6468547 | 51.571 | Myrcene |
| 14 | 12.685 | 4762 | 0.038 | |
| 15 | 12.746 | 3884 | 0.031 | |
| 16 | 13.064 | 52106 | 0.415 | |
| 17 | 13.204 | 48568 | 0.387 | |
| 18 | 13.274 | 105192 | 0.838 | Methyl butyl Isobutyrate |
| 19 | 13.586 | 36238 | 0.288 | Limonene |
| 20 | 13.797 | 3396 | 0.027 | |
| 21 | 13.938 | 26704 | 0.212 | |
| 22 | 14.149 | 4588 | 0.036 | |
| 23 | 14.333 | 8748 | 0.069 | |
| 24 | 14.520 | 1416 | 0.011 | |
| 25 | 14.602 | 16543 | 0.131 | |
| 26 | 14.879 | 17328 | 0.138 | |
| 27 | 15.087 | 7345 | 0.058 | |
| 28 | 15.212 | 931 | 0.007 | |
| 29 | 15.420 | 743 | 0.005 | |
| 30 | 15.506 | 3693 | 0.029 | |
| 31 | 15.722 | 3398 | 0.027 | |
| 32 | 15.801 | 10636 | 0.084 | |
| 33 | 16.009 | 5267 | 0.042 | |
| 34 | 16.069 | 2526 | 0.020 | |
| 35 | 16.244 | 25684 | 0.204 | |
| 36 | 16.624 | 3088 | 0.024 | |
| 37 | 16.793 | 10279 | 0.081 | |
| 38 | 16.915 | 3626 | 0.028 | |
| 39 | 17.427 | 1969 | 0.015 | |
| 40 | 17.673 | 67587 | 0.538 | |
| 41 | 18.248 | 2557 | 0.020 | |
| 42 | 18.354 | 1000 | 0.008 | |
| 43 | 18.423 | 691 | 0.005 | |
| 44 | 18.953 | 7042 | 0.056 | |
| 45 | 19.178 | 7410 | 0.059 | |
| 46 | 19.291 | 6033 | 0.048 | |
| 47 | 19.466 | 10779 | 0.085 | |
| 48 | 19.777 | 7142 | 0.056 | |
| 49 | 19.956 | 4956 | 0.039 | |
| 50 | 20.134 | 23743 | 0.189 | |
| 51 | 20.364 | 804 | 0.006 | |
| 52 | 20.742 | 2092 | 0.016 | |
| 53 | 20.877 | 5423 | 0.043 | |
| 54 | 20.984 | 1676 | 0.013 | |
| 55 | 21.043 | 923 | 0.007 | |
| 56 | 21.229 | 29717 | 0.236 | |
| 57 | 21.448 | 1539 | 0.012 | |
| 58 | 21.532 | 7494 | 0.059 | |
| 59 | 21.843 | 8179 | 0.065 | |
| 60 | 22.211 | 1838 | 0.014 | |
| 61 | 22.295 | 6856 | 0.054 | |
| 62 | 22.441 | 19924 | 0.158 | |
| 63 | 22.568 | 2933 | 0.023 | |
| 64 | 22.750 | 66342 | 0.528 | |
| 65 | 22.922 | 5479 | 0.043 | |
| 66 | 23.076 | 2236 | 0.017 | |
| 67 | 23.224 | 1919 | 0.015 | |
| 68 | 23.360 | 6240 | 0.049 | |
| 69 | 23.682 | 59058 | 0.470 | Linalool |
| 70 | 23.938 | 25935 | 0.206 | |
| 71 | 24.171 | 19672 | 0.156 | |
| 72 | 24.285 | 1535 | 0.012 | |
| 73 | 24.432 | 6320 | 0.050 | |
| 74 | 24.542 | 1797 | 0.014 | |
| 75 | 24.816 | 10688 | 0.085 | |
| 76 | 25.028 | 9189 | 0.073 | |
| 77 | 25.276 | 29524 | 0.235 | |
| 78 | 25.457 | 3016 | 0.024 | |
| 79 | 25.597 | 16721 | 0.133 | |
| 80 | 25.737 | 4624 | 0.036 | |
| 81 | 25.858 | 45802 | 0.365 | |
| 82 | 26.177 | 789857 | 6.297 | Caryophyllene |
| 83 | 26.267 | 147160 | 1.173 | |

APPENDIX 2-continued

Detailed GLC analyses of Columbus and other U.S. high alpha hops.

| | | | | |
|---|---|---|---|---|
| 84 | 26.483 | 11876 | 0.094 | |
| 85 | 26.654 | 2115 | 0.016 | |
| 86 | 26.951 | 19239 | 0.153 | |
| 87 | 27.128 | 7807 | 0.062 | |
| 88 | 27.262 | 34560 | 0.275 | Farnesene? |
| 89 | 27.452 | 5485 | 0.043 | |
| 90 | 27.650 | 12130 | 0.096 | |
| 91 | 27.741 | 32092 | 0.255 | |
| 92 | 28.029 | 22059 | 0.175 | |
| 93 | 28.286 | 1385879 | 11.049 | Humulene |
| 94 | 28.518 | 174316 | 1.389 | |
| 95 | 28.816 | 1217 | 0.009 | |
| 96 | 29.099 | 46594 | 0.371 | |
| 97 | 29.289 | 65255 | 0.520 | |
| 98 | 29.452 | 50235 | 0.400 | |
| 99 | 29.663 | 101538 | 0.809 | |
| 100 | 29.743 | 96334 | 0.768 | Muurolene |
| 101 | 29.922 | 184741 | 1.472 | Selinene |
| 102 | 30.066 | 2003 | 0.016 | Geranyl Acetate |
| 103 | 30.168 | 16997 | 0.135 | |
| 104 | 30.380 | 230089 | 1.834 | delta Cadinene |
| 105 | 30.604 | 137367 | 1.095 | Gamma Cadiene |
| 106 | 30.702 | 18692 | 0.149 | |
| 107 | 30.952 | 9850 | 0.078 | |
| 108 | 31.085 | 4796 | 0.038 | |
| 109 | 31.312 | 215300 | 1.716 | Geranyl Isobutyrate |
| 110 | 31.411 | 169139 | 1.348 | Undecanone-2 |
| 111 | 31.517 | 26715 | 0.213 | |
| 112 | 31.630 | 77466 | 0.617 | |
| 113 | 31.737 | 5913 | 0.047 | |
| 114 | 31.821 | 6115 | 0.048 | Geraniol |
| 115 | 32.106 | 9621 | 0.076 | |
| 116 | 32.224 | 20686 | 0.164 | |
| 117 | 32.501 | 13220 | 0.105 | |
| 118 | 32.620 | 30790 | 0.245 | |
| 119 | 33.031 | 7712 | 0.061 | |
| 120 | 33.254 | 2445 | 0.019 | |
| 121 | 33.462 | 7790 | 0.062 | |
| 122 | 33.722 | 28110 | 0.224 | |
| 123 | 33.960 | 4270 | 0.034 | |
| 124 | 34.081 | 2094 | 0.016 | |
| 125 | 34.192 | 4256 | 0.033 | |
| 126 | 34.312 | 4289 | 0.034 | |
| 127 | 34.372 | 5764 | 0.046 | |
| 128 | 34.483 | 5031 | 0.040 | |
| 129 | 34.565 | 5092 | 0.040 | |
| 131 | 34.901 | 34301 | 0.273 | |
| 132 | 35.009 | 13488 | 0.107 | |
| 133 | 35.126 | 5975 | 0.047 | |
| 134 | 35.299 | 1614 | 0.012 | |
| 135 | 35.487 | 11667 | 0.093 | |
| 136 | 35.854 | 17035 | 0.135 | Limonen-10-ol |
| 137 | 36.161 | 2233 | 0.017 | |
| 138 | 36.312 | 32546 | 0.259 | Caryophyllene oxide |
| 139 | 36.476 | 1067 | 0.008 | |
| 140 | 36.577 | 2462 | 0.019 | |
| 141 | 36.935 | 6949 | 0.055 | |
| 142 | 37.071 | 1073 | 0.008 | |
| 143 | 37.206 | 13125 | 0.104 | |
| 144 | 37.370 | 2081 | 0.016 | |
| 145 | 37.555 | 7101 | 0.056 | |
| 146 | 37.672 | 54047 | 0.430 | Humulene epoxide I |
| 147 | 38.006 | 8150 | 0.065 | |
| 148 | 38.127 | 3162 | 0.025 | |
| 149 | 38.444 | 2423 | 0.019 | |
| 150 | 38.688 | 30971 | 0.246 | |
| 151 | 38.915 | 181869 | 1.450 | Humulene epoxide II |
| 152 | 39.075 | 15063 | 0.120 | Caryolan-1-ol |
| 153 | 39.222 | 3225 | 0.025 | Humulene epoxide III |
| 154 | 39.501 | 7444 | 0.059 | |
| 155 | 39.809 | 1283 | 0.010 | |
| 156 | 39.935 | 1171 | 0.009 | |
| 157 | 40.158 | 5912 | 0.047 | |
| 158 | 40.396 | 1243 | 0.009 | |
| 159 | 40.677 | 52277 | 0.416 | |
| 160 | 40.871 | 8343 | 0.066 | |

APPENDIX 2-continued

Detailed GLC analyses of Columbus and other U.S. high alpha hops.

| | | | | |
|---|---|---|---|---|
| 161 | 41.254 | 6706 | 0.053 | |
| 162 | 41.404 | 23253 | 0.185 | Humulol |
| 163 | 41.759 | 4806 | 0.038 | |
| 164 | 41.946 | 30832 | 0.245 | |
| 165 | 42.077 | 2776 | 0.022 | |
| 166 | 42.236 | 2521 | 0.020 | |
| 167 | 42.537 | 2687 | 0.021 | |
| 168 | 42.964 | 11140 | 0.088 | |
| 169 | 43.065 | 7509 | 0.059 | |
| 170 | 43.258 | 23800 | 0.189 | |
| 171 | 43.848 | 4438 | 0.035 | |
| 172 | 44.637 | 12985 | 0.103 | Humulenol II |
| 173 | 45.039 | 5691 | 0.045 | |
| 174 | 45.892 | 3866 | 0.030 | |
| 175 | 46.597 | 1815 | 0.014 | |
| 176 | 47.014 | 2417 | 0.019 | |
| 177 | 50.412 | 1109 | 0.008 | |

= 1.25428E + 007

Area Percent Report
Sample Name: 92-12-8-3

| Pk # | Ret Time | Area | Area % | Identification |
|---|---|---|---|---|
| 1 | 7.034 | 2371 | 0.022 | |
| 2 | 7.855 | 753 | 0.007 | |
| 3 | 7.988 | 864 | 0.008 | |
| 4 | 8.623 | 706 | 0.066 | |
| 5 | 9.056 | 1684 | 0.016 | |
| 6 | 9.262 | 2429 | 0.023 | |
| 7 | 9.359 | 19367 | 0.184 | alpha Pinene |
| 8 | 9.801 | 6546 | 0.062 | |
| 9 | 10.096 | 924 | 0.008 | |
| 10 | 10.318 | 10977 | 0.104 | |
| 11 | 10.547 | 49458 | 0.469 | |
| 12 | 10.920 | 660 | 0.006 | |
| 13 | 11.098 | 1561 | 0.014 | |
| 14 | 11.242 | 93039 | 0.883 | beta Pinene |
| 15 | 11.733 | 1061 | 0.010 | |
| 16 | 11.901 | 3162 | 0.030 | |
| 17 | 12.090 | 1322 | 0.012 | |
| 18 | 12.484 | 6985773 | 66.360 | Myrcene |
| 19 | 12.692 | 7230 | 0.068 | |
| 20 | 12.750 | 5559 | 0.052 | |
| 21 | 13.073 | 155982 | 1.481 | |
| 22 | 13.217 | 83592 | 0.794 | |
| 23 | 13.301 | 376416 | 3.575 | Methylbutyl Isobutyrate |
| 24 | 13.593 | 36853 | 0.350 | Limoene |
| 25 | 13.810 | 1808 | 0.017 | |
| 26 | 13.942 | 30257 | 0.287 | |
| 27 | 14.151 | 2083 | 0.019 | |
| 28 | 14.317 | 15305 | 0.145 | |
| 29 | 14.529 | 2092 | 0.019 | |
| 30 | 14.609 | 73712 | 0.700 | |
| 31 | 14.896 | 239176 | 2.272 | |
| 32 | 15.091 | 5970 | 0.056 | |
| 33 | 15.333 | 699 | 0.006 | |
| 34 | 15.508 | 2556 | 0.024 | |
| 35 | 15.713 | 3795 | 0.036 | |
| 36 | 15.804 | 17078 | 0.162 | |
| 37 | 16.011 | 59153 | 0.561 | |
| 38 | 16.246 | 26755 | 0.254 | |
| 39 | 16.818 | 12944 | 0.123 | |
| 40 | 17.427 | 1728 | 0.016 | |
| 41 | 17.682 | 151069 | 1.435 | |
| 42 | 18.253 | 1689 | 0.016 | |
| 43 | 18.730 | 932 | 0.008 | |
| 44 | 18.953 | 1326 | 0.012 | |
| 45 | 19.192 | 122003 | 1.159 | |
| 46 | 19.329 | 5927 | 0.056 | |
| 47 | 19.481 | 11385 | 0.108 | |
| 48 | 19.791 | 7946 | 0.075 | |
| 49 | 19.952 | 1333 | 0.012 | |
| 50 | 20.134 | 5804 | 0.055 | |
| 51 | 20.727 | 9706 | 0.092 | |
| 52 | 20.879 | 21447 | 0.203 | |

APPENDIX 2-continued

Detailed GLC analyses of Columbus and other U.S. high alpha hops.

| | | | | |
|---|---|---|---|---|
| 53 | 21.054 | 2750 | 0.026 | |
| 54 | 21.227 | 17557 | 0.166 | |
| 55 | 21.769 | 2599 | 0.024 | |
| 56 | 22.298 | 42843 | 0.407 | |
| 57 | 22.437 | 4686 | 0.044 | |
| 58 | 22.494 | 4842 | 0.046 | |
| 59 | 22.739 | 15483 | 0.147 | |
| 60 | 22.234 | 720 | 0.006 | |
| 61 | 23.358 | 6212 | 0.059 | |
| 62 | 23.681 | 30996 | 0.294 | Linalool |
| 63 | 23.937 | 41114 | 0.390 | |
| 64 | 24.168 | 9021 | 0.085 | |
| 65 | 24.789 | 2293 | 0.021 | |
| 66 | 25.025 | 2599 | 0.024 | |
| 67 | 25.343 | 82950 | 0.788 | |
| 68 | 25.449 | 1561 | 0.014 | |
| 69 | 25.596 | 28078 | 0.266 | |
| 70 | 25.830 | 3277 | 0.031 | |
| 71 | 26.073 | 326058 | 3.097 | Caryophyllene |
| 72 | 26.267 | 160273 | 1.522 | |
| 73 | 26.482 | 8286 | 0.078 | |
| 74 | 26.695 | 887 | 0.008 | |
| 75 | 26.833 | 1478 | 0.014 | |
| 76 | 26.923 | 20836 | 0.197 | |
| 77 | 27.019 | 1307 | 0.012 | |
| 78 | 27.112 | 1737 | 0.016 | |
| 79 | 27.223 | 11802 | 0.112 | Farnesene? |
| 80 | 27.440 | 2763 | 0.026 | |
| 81 | 27.709 | 6688 | 0.063 | |
| 82 | 28.023 | 24366 | 0.231 | |
| 83 | 28.227 | 606830 | 5.764 | Humulene |
| 84 | 28.353 | 4325 | 0.041 | |
| 85 | 28.485 | 24982 | 0.237 | |
| 86 | 28.582 | 4950 | 0.047 | |
| 87 | 28.782 | 837 | 0.008 | |
| 88 | 29.082 | 8038 | 0.076 | |
| 89 | 29.251 | 9309 | 0.088 | |
| 90 | 29.429 | 7845 | 0.074 | |
| 91 | 29.642 | 32547 | 0.309 | Muurolene |
| 92 | 29.716 | 35968 | 0.341 | Selinene |
| 93 | 29.883 | 5145 | 0.048 | Geranyl Acetate |
| 94 | 30.139 | 3103 | 0.029 | |
| 95 | 30.328 | 30746 | 0.292 | delta Cadinene |
| 96 | 30.562 | 15061 | 0.143 | gamma Cadinene |
| 97 | 30.780 | 1170 | 0.011 | |
| 98 | 31.068 | 2479 | 0.023 | |
| 99 | 31.144 | 7554 | 0.071 | |
| 100 | 31.383 | 31189 | 0.296 | Geranyl Isobutyrate |
| 101 | 31.504 | 6271 | 0.059 | Undecanone-2 |
| 102 | 31.610 | 3590 | 0.034 | |
| 103 | 31.720 | 6384 | 0.060 | Geraniol |
| 104 | 32.097 | 2303 | 0.021 | |
| 105 | 32.222 | 1438 | 0.013 | |
| 106 | 32.489 | 10866 | 0.103 | |
| 107 | 32.608 | 3493 | 0.033 | |
| 108 | 33.028 | 780 | 0.007 | |
| 109 | 33.719 | 42378 | 0.402 | |
| 110 | 33.949 | 697 | 0.006 | |
| 111 | 34.181 | 786 | 0.007 | |
| 112 | 34.478 | 1455 | 0.013 | |
| 113 | 34.754 | 699 | 0.006 | |
| 114 | 34.891 | 1927 | 0.018 | |
| 115 | 35.004 | 1561 | 0.014 | |
| 116 | 35.121 | 616 | 0.005 | |
| 117 | 35.487 | 19190 | 0.182 | |
| 118 | 35.892 | 2261 | 0.021 | Limonen-10-ol |
| 119 | 36.302 | 1551 | 0.014 | Caryophyllene oxide |
| 120 | 37.203 | 2536 | 0.024 | |
| 121 | 37.660 | 3554 | 0.033 | Humulene epoxide I |
| 122 | 38.680 | 5605 | 0.053 | |
| 123 | 38.888 | 7257 | 0.068 | Humulene epoxide II |
| 124 | 39.082 | 690 | 0.006 | Caryolan-1-ol |
| 125 | 40.154 | 1386 | 0.013 | Humulene epoxide III |
| 126 | 40.669 | 3261 | 0.031 | |
| 127 | 40.872 | 1801 | 0.017 | |
| 128 | 41.248 | 3412 | 0.032 | |

APPENDIX 2-continued

Detailed GLC analyses of Columbus and other U.S. high alpha hops.

| | | | | |
|---|---|---|---|---|
| 129 | 41.399 | 1245 | 0.011 | Humulol |
| 130 | 41.937 | 4179 | 0.039 | |
| 131 | 43.258 | 1708 | 0.016 | |

Total area = 1.0527E + 007

Area Percent Report
Sample Name: 92-12-9-1

| Pk # | Ret Time | Area | Area % | Identification |
|---|---|---|---|---|
| 1 | 7.028 | 3603 | 0.029 | |
| 2 | 7.848 | 1142 | 0.009 | |
| 3 | 8.004 | 772 | 0.006 | |
| 4 | 9.048 | 3120 | 0.025 | |
| 5 | 9.253 | 7251 | 0.060 | |
| 6 | 9.351 | 5689 | 0.047 | alpha Pinene |
| 7 | 9.794 | 4017 | 0.033 | |
| 8 | 10.302 | 1522 | 0.012 | |
| 9 | 10.538 | 14530 | 0.120 | |
| 10 | 11.090 | 761 | 0.006 | |
| 11 | 11.231 | 52365 | 0.435 | beta Pinene |
| 12 | 11.886 | 700 | 0.005 | |
| 13 | 12.412 | 3424969 | 28.463 | Myrcene |
| 14 | 12.648 | 2525 | 0.021 | |
| 15 | 12.725 | 2971 | 0.024 | |
| 16 | 13.048 | 23622 | 0.196 | |
| 17 | 13.193 | 43283 | 0.359 | |
| 18 | 13.268 | 169688 | 1.410 | Methylbutyl Isobutyrate |
| 19 | 13.576 | 16461 | 0.136 | Limonene |
| 20 | 13.794 | 2031 | 0.016 | |
| 21 | 13.929 | 18137 | 0.150 | |
| 22 | 14.311 | 4573 | 0.038 | |
| 23 | 14.595 | 10186 | 0.084 | |
| 24 | 14.873 | 11403 | 0.094 | |
| 25 | 15.080 | 12395 | 0.103 | |
| 26 | 15.413 | 700 | 0.005 | |
| 27 | 15.501 | 899 | 0.007 | |
| 28 | 15.700 | 2332 | 0.019 | |
| 29 | 15.796 | 15536 | 0.129 | |
| 30 | 16.002 | 9137 | 0.075 | |
| 31 | 16.243 | 38778 | 0.322 | |
| 32 | 16.787 | 5760 | 0.047 | |
| 33 | 16.906 | 1286 | 0.010 | |
| 34 | 17.425 | 608 | 0.005 | |
| 35 | 17.676 | 114830 | 0.954 | |
| 36 | 18.247 | 625 | 0.005 | |
| 37 | 18.947 | 1621 | 0.013 | |
| 38 | 19.175 | 28172 | 0.234 | |
| 39 | 19.294 | 3311 | 0.027 | |
| 40 | 19.463 | 9984 | 0.083 | |
| 41 | 19.771 | 2700 | 0.022 | |
| 42 | 19.947 | 1731 | 0.014 | |
| 43 | 20.130 | 4426 | 0.036 | |
| 44 | 20.732 | 2604 | 0.021 | |
| 45 | 20.874 | 10809 | 0.089 | |
| 46 | 21.044 | 2047 | 0.017 | |
| 47 | 21.230 | 61271 | 0.509 | |
| 48 | 21.533 | 14424 | 0.119 | |
| 49 | 21.780 | 1521 | 0.012 | |
| 50 | 21.843 | 956 | 0.007 | |
| 51 | 22.211 | 2063 | 0.017 | |
| 52 | 22.293 | 15179 | 0.126 | |
| 53 | 22.443 | 32264 | 0.268 | |
| 54 | 22.570 | 3366 | 0.028 | |
| 55 | 22.756 | 106737 | 0.887 | |
| 56 | 23.080 | 5302 | 0.044 | |
| 57 | 23.356 | 6309 | 0.052 | |
| 58 | 23.680 | 44440 | 0.369 | Linalool |
| 59 | 23.941 | 75567 | 0.628 | |
| 60 | 24.170 | 15675 | 0.130 | |
| 61 | 24.434 | 2150 | 0.017 | |
| 62 | 24.524 | 1616 | 0.013 | |
| 63 | 24.806 | 7293 | 0.060 | |
| 64 | 25.028 | 2541 | 0.021 | |
| 65 | 25.278 | 37278 | 0.309 | |
| 66 | 25.346 | 31734 | 0.263 | |

APPENDIX 2-continued

Detailed GLC analyses of Columbus and other U.S. high alpha hops.

| | | | | |
|---|---|---|---|---|
| 67 | 25.605 | 32557 | 0.270 | |
| 68 | 25.881 | 90397 | 0.751 | |
| 69 | 26.140 | 1145130 | 9.516 | Caryophyllene |
| 70 | 26.269 | 176130 | 1.463 | |
| 71 | 26.486 | 9543 | 0.079 | |
| 72 | 26.835 | 1812 | 0.015 | |
| 73 | 26.988 | 22481 | 0.186 | |
| 74 | 27.140 | 17473 | 0.145 | |
| 75 | 27.353 | 42477 | 0.353 | Farnesene? |
| 76 | 27.473 | 5304 | 0.044 | |
| 77 | 27.783 | 61915 | 0.514 | |
| 78 | 28.035 | 24287 | 0.201 | |
| 79 | 28.343 | 2545867 | 21.157 | Humulene |
| 80 | 28.547 | 315497 | 2.622 | |
| 81 | 28.832 | 2334 | 0.019 | |
| 82 | 28.945 | 5985 | 0.049 | |
| 83 | 29.120 | 75042 | 0.623 | |
| 84 | 29.300 | 116317 | 0.966 | |
| 85 | 29.469 | 97160 | 0.807 | |
| 86 | 29.682 | 182550 | 1.517 | Muurolene |
| 87 | 29.764 | 166698 | 1.385 | Selinene |
| 88 | 29.967 | 25357 | 0.210 | Geranyl Acetate |
| 89 | 30.169 | 7062 | 0.058 | |
| 90 | 30.417 | 507237 | 4.215 | delta Cadiene |
| 91 | 30.630 | 323297 | 2.686 | gamma Cadiene |
| 92 | 30.879 | 5404 | 0.044 | |
| 93 | 31.069 | 10371 | 0.086 | |
| 94 | 31.155 | 5319 | 0.044 | |
| 95 | 31.332 | 399851 | 3.323 | Geranyl Isoburyrate |
| 96 | 31.467 | 81272 | 0.675 | Undecanone-2 |
| 97 | 31.617 | 7782 | 0.064 | |
| 98 | 31.730 | 18703 | 0.155 | Geraniol |
| 99 | 31.890 | 7540 | 0.062 | |
| 100 | 32.109 | 8984 | 0.074 | |
| 101 | 32.223 | 86628 | 0.719 | |
| 102 | 32.436 | 9265 | 0.077 | |
| 103 | 32.491 | 6647 | 0.055 | |
| 104 | 32.620 | 30270 | 0.251 | |
| 105 | 33.035 | 3306 | 0.027 | |
| 106 | 33.230 | 743 | 0.006 | |
| 107 | 33.464 | 4214 | 0.035 | |
| 108 | 33.728 | 87090 | 0.723 | |
| 109 | 33.951 | 2444 | 0.020 | |
| 110 | 34.183 | 3253 | 0.027 | |
| 111 | 34.370 | 4703 | 0.039 | |
| 112 | 34.480 | 4897 | 0.040 | |
| 113 | 34.758 | 3342 | 0.027 | |
| 114 | 34.896 | 11595 | 0.096 | |
| 115 | 35.007 | 14221 | 0.118 | |
| 116 | 35.299 | 1278 | 0.010 | |
| 117 | 35.489 | 39880 | 0.331 | |
| 118 | 35.873 | 5944 | 0.049 | Limonen-10-ol |
| 119 | 35.982 | 1196 | 0.009 | |
| 120 | 36.163 | 3016 | 0.025 | |
| 121 | 36.310 | 9199 | 0.076 | Caryophyllene oxide |
| 122 | 36.564 | 1474 | 0.012 | |
| 123 | 36.871 | 5580 | 0.046 | |
| 124 | 37.205 | 13593 | 0.113 | |
| 125 | 37.365 | 21562 | 0.179 | |
| 126 | 37.551 | 3095 | 0.025 | |
| 127 | 37.669 | 39322 | 0.326 | Humulene epoxide I |
| 128 | 37.863 | 1467 | 0.012 | |
| 129 | 38.004 | 7647 | 0.063 | |
| 130 | 38.124 | 2074 | 0.017 | |
| 131 | 38.438 | 1793 | 0.014 | |
| 132 | 38.685 | 50800 | 0.422 | |
| 133 | 38.900 | 79889 | 0.663 | Humulene epoxide II |
| 134 | 39.082 | 10671 | 0.088 | Caryolan-1-ol |
| 135 | 39.209 | 4042 | 0.033 | Humulene epoxide III |
| 136 | 39.500 | 2852 | 0.023 | |
| 137 | 39.716 | 694 | 0.005 | |
| 138 | 39.789 | 600 | 0.005 | |
| 139 | 40.149 | 3072 | 0.025 | |
| 140 | 40.465 | 1310 | 0.010 | |
| 141 | 40.672 | 16151 | 0.134 | |
| 142 | 40.874 | 13029 | 0.108 | |

APPENDIX 2-continued

Detailed GLC analyses of Columbus and other U.S. high alpha hops.

| | | | | |
|---|---|---|---|---|
| 143 | 41.250 | 10136 | 0.084 | |
| 144 | 41.406 | 45643 | 0.379 | Humulol |
| 145 | 41.758 | 11528 | 0.095 | |
| 146 | 41.846 | 13183 | 0.109 | |
| 147 | 41.945 | 25814 | 0.214 | |
| 148 | 42.073 | 9818 | 0.081 | |
| 149 | 42.534 | 5222 | 0.043 | |
| 150 | 42.964 | 29878 | 0.248 | beta Eudesmol? |
| 151 | 43.065 | 24765 | 0.205 | alpha Eudesmol? |
| 152 | 43.255 | 33781 | 0.280 | |
| 153 | 43.565 | 1828 | 0.015 | |
| 154 | 43.846 | 10003 | 0.083 | |
| 155 | 44.289 | 5485 | 0.045 | |
| 156 | 44.370 | 3097 | 0.025 | |
| 157 | 44.633 | 13527 | 0.112 | Humulenol II |
| 158 | 45.042 | 12525 | 0.104 | |
| 159 | 45.700 | 38097 | 0.316 | Humulene diepoxide? |
| 160 | 45.885 | 3830 | 0.031 | |
| 161 | 46.615 | 2140 | 0.017 | |
| 162 | 47.030 | 2967 | 0.024 | |
| 163 | 48.254 | 4136 | 0.034 | |
| 164 | 48.524 | 1729 | 0.014 | |
| 165 | 52.198 | 1275 | 0.010 | |

Total area = 1.20327E + 007

Area Percent Report
Sample Name: 92-12-9-2

| Pk # | Ret Time | Area | Area % | Identification |
|---|---|---|---|---|
| 1 | 7.034 | 1627 | 0.013 | |
| 2 | 7.850 | 1222 | 0.010 | |
| 3 | 9.051 | 1362 | 0.011 | |
| 4 | 9.259 | 2214 | 0.018 | |
| 5 | 9.355 | 9693 | 0.081 | alpha Pinene |
| 6 | 9.796 | 3741 | 0.031 | |
| 7 | 10.309 | 1970 | 0.016 | |
| 8 | 10.542 | 19685 | 0.166 | |
| 9 | 11.093 | 943 | 0.008 | |
| 10 | 11.236 | 79174 | 0.667 | beta Pinene |
| 11 | 11.895 | 2296 | 0.019 | |
| 12 | 12.468 | 6160576 | 51.972 | Myrcene |
| 13 | 12.679 | 3749 | 0.031 | |
| 14 | 12.741 | 4270 | 0.036 | |
| 15 | 13.058 | 44822 | 0.378 | |
| 16 | 13.201 | 59258 | 0.499 | |
| 17 | 13.275 | 151104 | 1.274 | Methylbutyl Isobutyrate |
| 18 | 13.582 | 21713 | 0.183 | Limonene |
| 19 | 13.800 | 1814 | 0.015 | |
| 20 | 13.934 | 28562 | 0.241 | |
| 21 | 14.144 | 933 | 0.007 | |
| 22 | 14.311 | 6730 | 0.056 | |
| 23 | 14.519 | 2088 | 0.017 | |
| 24 | 14.609 | 6243 | 0.052 | |
| 25 | 14.875 | 55333 | 0.466 | |
| 26 | 15.083 | 3970 | 0.033 | |
| 27 | 15.326 | 1045 | 0.008 | |
| 28 | 15.416 | 636 | 0.005 | |
| 29 | 15.503 | 2028 | 0.017 | |
| 30 | 15.702 | 2642 | 0.022 | |
| 31 | 15.798 | 10210 | 0.086 | |
| 32 | 16.005 | 54321 | 0.458 | |
| 33 | 16.241 | 21435 | 0.180 | |
| 34 | 16.809 | 7970 | 0.067 | |
| 35 | 17.438 | 1939 | 0.016 | |
| 36 | 17.655 | 61020 | 0.514 | |
| 37 | 17.783 | 1252 | 0.010 | |
| 38 | 18.248 | 665 | 0.005 | |
| 39 | 18.948 | 1086 | 0.009 | |
| 40 | 19.179 | 60530 | 0.510 | |
| 41 | 19.314 | 1798 | 0.015 | |
| 42 | 19.462 | 8464 | 0.071 | |
| 43 | 19.546 | 4332 | 0.036 | |
| 44 | 19.785 | 6451 | 0.054 | |
| 45 | 19.949 | 1390 | 0.011 | |
| 46 | 20.130 | 4840 | 0.040 | |

APPENDIX 2-continued

Detailed GLC analyses of Columbus and other U.S. high alpha hops.

| | | | | |
|---|---|---|---|---|
| 47 | 20.722 | 11806 | 0.099 | |
| 48 | 20.873 | 1283 | 0.010 | |
| 49 | 20.945 | 2757 | 0.023 | |
| 50 | 21.226 | 4405 | 0.037 | |
| 51 | 21.524 | 2418 | 0.020 | |
| 52 | 21.776 | 2520 | 0.021 | |
| 53 | 22.199 | 1123 | 0.009 | |
| 54 | 22.294 | 37518 | 0.316 | |
| 55 | 22.438 | 12669 | 0.106 | |
| 56 | 22.558 | 1478 | 0.012 | |
| 57 | 22.743 | 43371 | 0.365 | |
| 58 | 23.076 | 1222 | 0.010 | |
| 59 | 23.236 | 1059 | 0.008 | |
| 60 | 23.355 | 8797 | 0.074 | |
| 61 | 23.681 | 121220 | 1.022 | Linalool |
| 62 | 23.935 | 17913 | 0.151 | |
| 63 | 24.167 | 9930 | 0.083 | |
| 64 | 24.417 | 1477 | 0.012 | |
| 65 | 24.798 | 946 | 0.008 | |
| 66 | 24.923 | 911 | 0.007 | |
| 67 | 25.023 | 2303 | 0.019 | |
| 68 | 25.347 | 50189 | 0.423 | |
| 69 | 25.462 | 730 | 0.006 | |
| 70 | 25.605 | 63484 | 0.535 | |
| 71 | 25.731 | 14566 | 0.122 | |
| 72 | 25.863 | 19067 | 0.160 | |
| 73 | 26.129 | 1019106 | 8.597 | Caryophyllene |
| 74 | 26.267 | 172193 | 1.452 | |
| 75 | 26.484 | 13509 | 0.114 | |
| 76 | 26.649 | 3488 | 0.029 | |
| 77 | 26.830 | 1518 | 0.012 | |
| 78 | 26.973 | 2085 | 0.017 | |
| 79 | 37.057 | 3159 | 0.026 | |
| 80 | 27.127 | 4597 | 0.038 | |
| 81 | 27.284 | 19285 | 0.162 | Farnesene? |
| 82 | 27.452 | 4597 | 0.038 | |
| 83 | 27.558 | 1014 | 0.008 | |
| 84 | 27.766 | 17735 | 0.149 | |
| 85 | 28.030 | 20185 | 0.170 | |
| 86 | 28.324 | 2255638 | 19.029 | Humulene |
| 87 | 28.509 | 62699 | 0.529 | |
| 88 | 28.575 | 78837 | 0.665 | |
| 89 | 28.933 | 16176 | 0.136 | |
| 90 | 29.101 | 26411 | 0.222 | |
| 91 | 29.319 | 43633 | 0.368 | |
| 92 | 29.442 | 23012 | 0.194 | |
| 93 | 29.658 | 109275 | 0.921 | Muurolene |
| 94 | 29.741 | 97039 | 0.818 | Selinene |
| 95 | 29.881 | 5248 | 0.044 | Geranyl Acetate |
| 96 | 30.142 | 4602 | 0.038 | |
| 97 | 30.351 | 109776 | 0.926 | delta Cadinene |
| 98 | 30.580 | 52832 | 0.445 | gamma Cadinene |
| 99 | 30.771 | 1506 | 0.012 | |
| 100 | 30.851 | 1737 | 0.014 | |
| 101 | 31.082 | 5775 | 0.048 | |
| 102 | 31.205 | 11532 | 0.097 | |
| 103 | 31.330 | 9041 | 0.076 | Geranyl isobutyrate |
| 104 | 31.511 | 53799 | 0.453 | Undecanone-2 |
| 105 | 31.717 | 9415 | 0.079 | Geraniol |
| 106 | 31.814 | 3048 | 0.025 | |
| 107 | 32.085 | 5681 | 0.047 | |
| 108 | 32.219 | 5853 | 0.049 | |
| 109 | 32.492 | 1416 | 0.011 | |
| 110 | 32.608 | 7265 | 0.061 | |
| 111 | 33.033 | 906 | 0.007 | |
| 112 | 33.253 | 722 | 0.006 | |
| 113 | 33.712 | 10903 | 0.092 | |
| 114 | 33.945 | 1308 | 0.011 | |
| 115 | 34.071 | 2438 | 0.020 | |
| 116 | 34.181 | 1069 | 0.009 | |
| 117 | 34.368 | 5360 | 0.045 | |
| 118 | 34.474 | 674 | 0.005 | |
| 119 | 34.889 | 9616 | 0.081 | |
| 120 | 35.001 | 4520 | 0.038 | |
| 121 | 35.481 | 8543 | 0.072 | |
| 122 | 35.853 | 4382 | 0.037 | Limonen 10-ol |

APPENDIX 2-continued

Detailed GLC analyses of Columbus and other U.S. high alpha hops.

| | | | | |
|---|---|---|---|---|
| 123 | 35.976 | 1266 | 0.010 | |
| 124 | 36.154 | 1163 | 0.009 | |
| 125 | 36.296 | 3788 | 0.032 | Caryophyllene oxide |
| 126 | 36.909 | 1692 | 0.014 | |
| 127 | 37.183 | 9203 | 0.077 | |
| 128 | 37.358 | 1754 | 0.014 | |
| 129 | 37.660 | 26083 | 0.220 | Humulene epoxide I |
| 130 | 37.996 | 2405 | 0.020 | |
| 131 | 38.673 | 14395 | 0.121 | |
| 132 | 38.889 | 38989 | 0.328 | Humulene epoxide II |
| 133 | 39.079 | 1867 | 0.015 | Caryolan-1 ol |
| 134 | 39.922 | 885 | 0.007 | |
| 135 | 40.138 | 1296 | 0.010 | |
| 136 | 40.666 | 11481 | 0.096 | |
| 137 | 40.870 | 4099 | 0.034 | |
| 138 | 41.245 | 7744 | 0.065 | |
| 139 | 41.397 | 4776 | 0.040 | Humulol |
| 140 | 41.934 | 9925 | 0.083 | |
| 141 | 43.059 | 2394 | 0.020 | |

APPENDIX 2-continued

Detailed GLC analyses of Columbus and other U.S. high alpha hops.

| | | | | |
|---|---|---|---|---|
| 142 | 43.254 | 5249 | 0.044 | |
| 143 | 43.842 | 1927 | 0.016 | |
| 144 | 44.637 | 2619 | 0.022 | Humulenol II |

= 1.18535E + 007

| Reference: | Code | Variety |
|---|---|---|
| | 92-12-8-2 | Columbus |
| | 92-12-8-3 | Galena |
| | 92-12-9-1 | Chinook |
| | 92-12-9-2 | Nugget |

Analytical Conditions: See, Nickerson and van Engel, "Hop Aroma Component Profile and the Aroma Unit," Journal American Society of Brewing Chemists, 50(3), 77-82(1992).

What is claimed is:

1. A new and distinct variety of hop plant named Columbus, substantially as shown and described.

* * * * *